US006476078B2

(12) United States Patent
Jerussi et al.

(10) Patent No.: US 6,476,078 B2
(45) Date of Patent: Nov. 5, 2002

(54) METHODS OF USING SIBUTRAMINE METABOLITES IN COMBINATION WITH A PHOSPHODIESTERASE INHIBITOR TO TREAT SEXUAL DYSFUNCTION

(75) Inventors: Thomas P. Jerussi, Framingham; Chrisantha H. Senanayake, Shrewsbury; Qun K. Fang, Wellesley, all of MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/770,663

(22) Filed: Jan. 29, 2001

(65) Prior Publication Data

US 2002/0010198 A1 Jan. 24, 2002

Related U.S. Application Data

(63) Continuation-in-part of application No. 09/662,135, filed on Sep. 14, 2000, now Pat. No. 6,339,106, which is a continuation-in-part of application No. 09/372,158, filed on Aug. 11, 1999, now Pat. No. 6,331,571.

(51) Int. Cl.$^7$ .................. A61K 31/135; A61K 31/505; A61K 31/44; A61K 31/415; A61K 31/40
(52) U.S. Cl. .................. 514/646; 514/258; 514/283; 514/334; 514/394; 514/424
(58) Field of Search .................. 514/646, 258, 514/283, 334, 394, 424

(56) References Cited

U.S. PATENT DOCUMENTS

| | | | |
|---|---|---|---|
| 3,155,669 A | 11/1964 | Janssen et al. | |
| 3,155,670 A | 11/1964 | Janssen et al. | 260/294 |
| 3,471,515 A | 10/1969 | Troxler et al. | 260/326.15 |
| 3,536,809 A | 10/1970 | Applezweig | 424/28 |
| 3,598,123 A | 8/1971 | Zaffaroni | 128/268 |
| 3,845,770 A | 11/1974 | Theeuwes et al. | 128/260 |
| 3,916,899 A | 11/1975 | Theeuwes et al. | 128/260 |
| 3,960,891 A | 6/1976 | Malen et al. | 260/327 |
| 4,008,719 A | 2/1977 | Theeuwes et al. | 128/260 |
| 4,522,828 A | 6/1985 | Jeffery et al. | 514/646 |
| 4,552,828 A | 11/1985 | Toya et al. | 430/217 |
| 4,746,680 A | 5/1988 | Jeffery et al. | 514/646 |
| 4,806,570 A | 2/1989 | Jeffery et al. | 514/646 |
| 4,814,352 A | 3/1989 | Jeffery et al. | 514/646 |
| 4,816,488 A | 3/1989 | Rees | 514/646 |
| 4,871,774 A | 10/1989 | Rees | 514/646 |
| 4,929,629 A | 5/1990 | Jeffery | 514/646 |
| 4,939,175 A | 7/1990 | Ukai et al. | 514/646 |
| 4,988,814 A | 1/1991 | Abou-Gharbia et al. | 544/295 |
| 5,059,595 A | 10/1991 | Le Grazie | 424/468 |
| 5,068,440 A | 11/1991 | Jeffery et al. | 564/442 |
| 5,073,543 A | 12/1991 | Marshall et al. | 514/21 |
| 5,104,899 A | 4/1992 | Young et al. | 514/646 |
| 5,120,548 A | 6/1992 | McClelland et al. | 424/473 |
| 5,250,534 A | 10/1993 | Bell et al. | 514/258 |
| 5,354,556 A | 10/1994 | Sparks et al. | 424/419 |
| 5,436,272 A | 7/1995 | Scheinbaum | 514/646 |
| 5,459,164 A | 10/1995 | Vargas | 514/646 |
| 5,552,429 A | 9/1996 | Wong et al. | 514/415 |
| 5,591,767 A | 1/1997 | Mohr et al. | 514/413 |
| 5,639,476 A | 6/1997 | Oshlack et al. | 424/468 |
| 5,674,553 A | 10/1997 | Shinoda et al. | 427/68 |
| 5,719,283 A | 2/1998 | Bell et al. | 544/262 |
| 5,733,566 A | 3/1998 | Lewis | 424/426 |
| 5,780,051 A | 7/1998 | Eswara et al. | 424/449 |
| 5,795,880 A | 8/1998 | Svec et al. | 514/169 |
| 6,127,363 A | 10/2000 | Doherty et al. | 514/220 |

FOREIGN PATENT DOCUMENTS

| | | |
|---|---|---|
| DE | 32 12 682 A1 | 10/1982 |
| EP | 0 035 597 | 9/1981 |
| EP | 0 781 561 A1 | 7/1997 |
| GB | 2098602 A | 11/1982 |
| WO | WO 88/06444 | 9/1988 |
| WO | WO 90/06110 | 6/1990 |
| WO | WO 94/00047 | 1/1994 |
| WO | WO 94/00114 | 1/1994 |
| WO | WO 94/28902 | 12/1994 |
| WO | WO 95/20949 | 8/1995 |
| WO | WO 95/21615 | 8/1995 |
| WO | WO 97/03675 | 2/1997 |
| WO | WO 97/20810 | 6/1997 |
| WO | WO 98/06722 | 2/1998 |
| WO | WO 98/11884 | 3/1998 |
| WO | WO 98/13033 | 4/1998 |
| WO | WO 98/13034 | 4/1998 |
| WO | WO 99/33450 | 7/1999 |

OTHER PUBLICATIONS

Baldessarini et al., Life Sciences 39: 1765–1777, (1986).
Buckett et al., "BTS 54 524–An Approach to Rapidly Acting Antidepressant," New Concepts in Depression 2: 167–172 (1988).
Bucket et al., "The Pharmacology of Sibutramine Hydrochloride (BTS 54 524), A New Antidepressant which induces Rapid Noradrenergic Down–Regulation", Prog. Neuro–Psychopharmacol. & Biol. Psychiat. 12: 575–584 (1988).
Buckett et al., "Sibutramine Hydrochloride," Drugs of the Future 13(8): 736–738 (1988).
Butler, D., Facile Cycloalkylation of Arylacetonitriles in Dimethyl Sulfoxide, J. Org. Chem., 36:1308–1309 (1971).
Cannone, P., et al., Effet du Benzene Dans la Reaction de Grignard sur les Nitriles, Tetrahedron Lett., 21:155–58 (1980).
Carstensen, J., Drug Stability: Principles & Practice, 2d. Ed., pp. 379–380, Marcel Dekker, NY, NY, (1995).
Castello, R.A., et al., Discoloration of Tablets Containing Amines and Lactose, Pharm. Sci. 51(2):106–108 (1962).

(List continued on next page.)

Primary Examiner—William R. A. Jarvis
(74) Attorney, Agent, or Firm—Pennie & Edmonds LLP

(57) ABSTRACT

Methods are disclosed for the treatment and prevention of male and female sexual function disorders which comprise a racemic or optically pure sibutramine metabolite and a phosphodiesterase inhibitor.

12 Claims, No Drawings

OTHER PUBLICATIONS

Cheetham, S.C., et al., [³H]Paroxetine Binding in Rat Frontal Cortex Strongly Correlates with [³H]5–HT Cliffe et al., (S)–N–tert–Butyl–3–(4– (2–methoxyphenyl)–piperazin–1–yl)–2–phenylpropanamide [(S)–WAY–100135]: A Selective Antagonist at Presynaptic and Postsynaptic 5–HT$_{1A}$ Receptors, Med. Chem., 36:1509–1510 (1993).

*Diagnostic and Statistical Manual of Mental Disorders,* Fourth Ed., American Psychiatric Association, (1997).

*Diagnostic and Statistical Manual of Mental Disorders,* 3rd Ed., American Psychiatric Association (1981).

Dreshfield et al., Enhancement of Fluoxetine–Dependent Increase of Extracellular Serotonin (5–HT) Levels by (–)–Pindolol, an Antagonist at 5–HT$_{1A}$ Receptors, Neurochem. Res., 21(5):557–562 (1996).

Eliel, E.L., *Stereochemistry of Carbon Compounds* (McGraw–Hill, NY, 1962).

Evans et al., "Prevalance of Alzheimer's Disease in a Community Population of Older Persons," *J.A.M.A.* 262:2551–2556 (1989).

Fuentes, J.et al., "Comparison of the apparent anti–depressant activity of (–) and (+) tranylpromine in an animal model", *Chemical Abstracts,* 85: 7, p. 31, No. 40768t (1976).

Goodman & Gilman, The Pharmacological Basis of Therapeutics, 362–373, 404 (9$^{th}$ ed. McGraw–Hill, 1996).

Gray et al., *The Involvement of the Opioidergic System in the Antinociceptive Mechanism of Action of Antidepressant Compounds,* BR.J. Pharmacol., vol. 124, No. 4, (1988) pp. 669–674.

Handbook of Pharmaceutical Excipients, 2nd ed., Wade and Willer eds., pp. 257–259 (1994).

Heal et al., A Comparison of the Effects on Central 5–HT Function of Sibutramine Hydrochloride and Other Weight–Modifying Agents, Br.J. Pharmacol. (1998), 125(2), 301–308.

Hillyer et al., (S)–5–Fluoro–8–hydroxy–2–(dipropylamino)tetralix: A Putative 5–HT$_{1A}$ Receptor Antagonist, J. Med. Chem., 33:1541–44 (1990).

J. Med. Chem., vol. 36, No. 17, 2540 (1993).

*Introduction to Pharmaceutical Dosage Forms,* 4th ed., Lea & Febiger, Philadelphia (1985).

Jacques et al., "Enantiomers, Racemates and Resolutions," Wiley–Interscience, NY, 1981).

Jamali et al., *Journal of Pharmaceutical Science,* 78: 9: 695–715 (1989).

Jeffery et al., Synthesis of Sibutramine, A Novel Cyclobutylalkylamine Useful in the Treatment of Obesity, and its Major Human Metabolites, J. Chem. Soc. Perkin. Trans. 1, 2583–2589 (1996).

King et al., "Clinical Pharmacology of Sibutramine Hydrochloride (BTS 54524) A New Antidepressant, in Healthy Volunteers," *Clinical Pharmac.* 26: 607–611 (1989).

Kula et al., "Effects of N–Subsituted Phenyltetrahydropyridines on Cerebral High–Affinity Synatosomal Uptake of Dopamine and Other Monoamines in Several Mammalian Species," *Life Sciences* 34(26):2567–2575, (1984).

Luscombe et al., The Contribution of Metabolites to the Rapid and Potent Down–Regulation of Rat Cortical β–Adrenoceptors by the Putative Antidepressant Sibutramine Hydrochloride, Neuropharmacology, vol. 28, No. 2, (1989) pp. 129–134.

The Merck Manual of Diagnosis and Therpay, 17th Ed., Merck & Co., Inc., Whitehouse Station, NJ, (1999).

Middlemiss et al., Centrally Active 5–HT Receptor Agonists and Antagonists, Neurosci. and Biobehv. Rev., 16:75–82 (1992).

Moreau et al., Behavioral Profile of the 5–HT$_{1A}$ Receptor Antagonist (S)–UH–301 in Rodents and Monkeys, Brain Res. Bull., 29:901–04 (1992).

Nakada et al., An Enantioconvergent Route to (–)–Kainic Acid, Tetrahedron Lett., 38:857–860 (1997).

*Physician's Desk Reference®* 473–475 (53$^{rd}$ ed., 1999).
*Physician's Desk Reference®* 475–476 (53$^{rd}$ ed., 1999).
*Physician's Desk Reference®* 764–766 (53$^{rd}$ ed., 1999).
*Physician's Desk Reference®* 823–825 (53$^{rd}$ ed., 1999).
*Physician's Desk Reference®* 978–979 (53$^{rd}$ ed., 1999).
*Physician's Desk Reference®* 1054–1056 (53$^{rd}$ ed., 1999).
*Physician's Desk Reference®* 1332–1334 (53$^{rd}$ ed., 1999).
*Physician's Desk Reference®* 1369–1370 (53$^{rd}$ ed., 1999).
*Physician's Desk Reference®* 1432–1436 (53$^{rd}$ ed., 1999).
*Physician's Desk Reference®* 1494–1498 (53$^{rd}$ ed., 1999).
*Physician's Desk Reference®* 1641–1645 (53$^{rd}$ ed., 1999).
*Physician's Desk Reference®* 2004–2009 (53$^{rd}$ ed., 1999).
*Physician's Desk Reference®* 2075–2078 (53$^{rd}$ ed., 1999).
*Physician's Desk Reference®* 2190–2192 (53$^{rd}$ ed., 1999).
*Physician's Desk Reference®* 2367–2368 (53$^{rd}$ ed., 1999).
*Physician's Desk Reference®* 2396–2399 (53$^{rd}$ ed., 1999).
*Physician's Desk Reference®* 2490–2493 (53$^{rd}$ ed., 1999).
*Physician's Desk Reference®* 2516–2521 (53$^{rd}$ ed., 1999).
*Physician's Desk Reference®* 2688–2691 (53$^{rd}$ ed., 1999).
*Physician's Desk Reference®* 2701–2704 (53$^{rd}$ ed., 1999).
*Physician's Desk Reference®* 2720–2726 (53$^{rd}$ ed., 1999).
*Physician's Desk Reference®* 2735–2736 (53$^{rd}$ ed., 1999).
*Physician's Desk Reference®* 2886–2888 (53$^{rd}$ ed., 1999).
*Physician's Desk Reference®* 2908–2910 (53$^{rd}$ ed., 1999).
*Physician's Desk Reference®* 3092–3094 (53$^{rd}$ ed., 1999).
*Physician's Desk Reference®* 3101–3104 (53$^{rd}$ ed., 1999).
*Physician's Desk Reference®* 3224–3225 (53$^{rd}$ ed., 1999).
*Physician's Desk Reference®* 3267–3272 (53$^{rd}$ ed., 1999).
*Physician's Desk Reference®* 3307–3309 (53$^{rd}$ ed., 1999).
*Physician's Desk Reference®* 3383–3384 (53$^{rd}$ ed., 1999).
*Physician's Desk Reference®* 2520 (52$^{rd}$ ed., 1998).
*Physician's Desk Reference®* 2958 (52$^{rd}$ ed., 1998).

*Remingtons: The Practice of TheScience and Pharmacy,* 19$^{th}$ ed., Gennaro, ed., p. 1625 (1995).

*Remington's Pharmaceutical Sciences,* 18th ed., Mack Publishing, Easton PA (1990).

*Remington's Pharmaceutical Sciences,* 16th ed., Mack Publishing, Easton PA (1980).

Stock, M.J., Sibutramine: A Review of the Pharmacology of a Novel Anti–Obesity Agent, Int'l J. Obesity, 21(Supp. 1):S25–S29 (1997).

Wilen et al., *Tetrahedron,* 2725–36 33(21) (1977).

Wilen, S.H., Tables of Resolving Agents and Optical Resolutions 268 (E.L. Eliel ed., Univ. of Notre Dame Press, Notre Dame, IN, 1972).

METHODS OF USING SIBUTRAMINE METABOLITES IN COMBINATION WITH A PHOSPHODIESTERASE INHIBITOR TO TREAT SEXUAL DYSFUNCTION

This application is a continuation-in-part of U.S. application Ser. No. 09/662,135, filed Sep. 14, 2000, now U.S. Pat. No. 6,339,106, which is a continuation-in-part of U.S. application Ser. No. 09/372,158, filed Aug. 11, 1999, now U.S. Pat. No. 6,331,571 both of which are incorporated herein by reference in their entireties.

FIELD OF THE INVENTION

The invention relates to methods of using and compositions comprising dopamine reuptake inhibitors such as racemic and optically pure metabolites of sibutramine, optionally in combination with other pharmacologically active compounds.

BACKGROUND OF THE INVENTION

Sibutramine, chemically named [N-1-[1-(4-chlorophenyl)cyclobutyl]-3-methylbutyl]-N,N-dimethylamine, is a neuronal monoamine reuptake inhibitor which was originally disclosed in U.S. Pat. Nos. 4,746,680 and 4,806,570. Sibutramine inhibits the reuptake of norepinephrine and, to a lesser extent, serotonin and dopamine. See, e.g., Buckett et al., *Prog. Neuro-psychopharm. & Biol. Psychiat.*, 12:575–584, 1988; King et al., *J. Clin. Pharm.*, 26:607–611 (1989).

Racemic sibutramine is sold as a hydrochloride monohydrate under the tradename MERIDIA®, and is indicated for the treatment of obesity. *Physician's Desk References* 1494–1498 (53$^{rd}$ ed., 1999). The treatment of obesity using racemic sibutramine is disclosed, for example, in U.S. Pat. No. 5,436,272.

Sibutramine appears to have been extensively studied, and reportedly could be used in the treatment of a variety of disorders. For example, U.S. Pat. Nos. 4,552,828, 4,746,680, 4,806,570, and 4,929,629 disclose methods of treating depression using racemic sibutramine, and U.S. Pat. Nos. 4,871,774 and 4,939,175 disclose methods of treating Parkinson's disease and senile dementia, respectively, using racemic sibutramine. Other uses of sibutramine are disclosed by PCT publications WO 95/20949, WO 95/21615, WO 98/11884, and WO 98/13033. Further, the optically pure entantiomers of sibutramine have been considered for development. For example, PCT publications WO 94/00047 and 94/00114 disclose methods of treating depression and related disorders using the (R)- and (S)-enantiomers of sibutramine, respectively.

Sibutramine is rapidly absorbed from the gastrointestinal tract following oral administration and undergoes an extensive first-pass metabolism that yields the primary metabolites, desmethylsibutramine and didesmethylsibutramine, shown below.

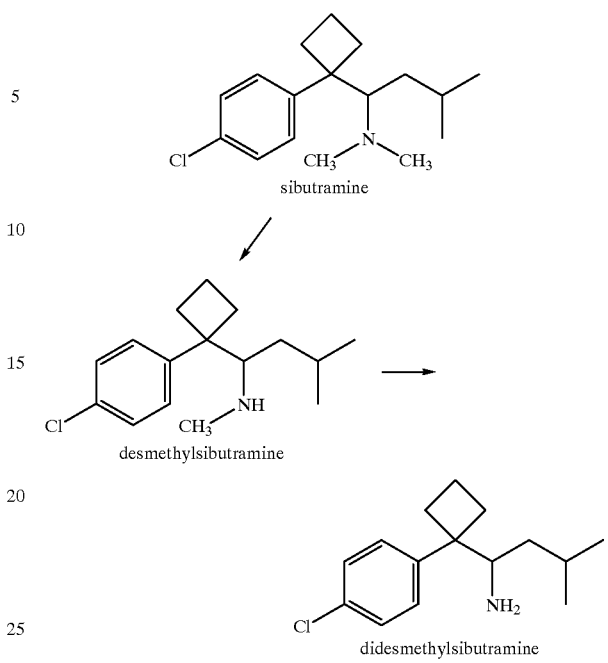

It has been reported that desmethylsibutramine and didesmethylsibutramine are more potent in vitro noradrenaline and 5-hydroxytryptamine (5HT; serotonin) reuptake inhibitors than sibutramine. Stock, M. J., *Int'l J. Obesity*, 21(Supp. 1):S25-S29 (1997). It has further been reported, however, that sibutramine and its metabolites have negligible affinities for a wide range of neurotransmitter receptors, including serotonergic (5-HT$_1$, 5-HT$_{1A}$, 5-HT$_{1D}$, 5-HT$_{2A}$, 5-HT$_{2C}$), adrenergic, dopaminergic, muscarinic, histaminergic, glutamate, and benzodiazepine receptors. Id.

Sibutramine has a variety of adverse effects. See, e.g., *Physician's Desk Reference®* 1494–1498 (53$^{rd}$ ed., 1999). Coupled with the reported benefits and therapeutic insufficiencies of sibutramine, this fact has encouraged the discovery of compounds and compositions that can be used in the treatment or prevention of disorders such as, but not limited to, sexual (e.g., erectile) dysfunction, affective disorders, weight gain or obesity, cerebral function disorders, pain, obsessive-compulsive disorder, substance abuse, chronic disorders, anxiety, eating disorders, migraines, and incontinence. In particular, compounds and compositions are desired that can be used for the treatment and prevention of such disorders and conditions while incurring fewer of the adverse effects associated with sibutramine.

SUMMARY OF THE INVENTION

This invention encompasses methods of treating and preventing disorders and conditions that are ameliorated by the inhibition of neuronal monoamine uptake, which comprise administering to a patient in need of such treatment or prevention a therapeutically or prophylactically effective amount of a neuronal monoamine reuptake inhibitor. Preferred neuronal monoamine reuptake inhibitors are sibutramine metabolites. In specific methods of the invention, the neuronal monoamine reuptake inhibitor is optionally administered in combination with an additional pharmacologically active compound.

Examples of disorders and conditions that are ameliorated by the inhibition of neuronal monoamine uptake include, but are not limited to: eating disorders; weight gain; obesity; irritable bowel syndrome; obsessive-compulsive disorders; platelet adhesion; apnea; affective disorders such as attention deficit disorders, depression, and anxiety; male and female sexual function disorders; restless leg syndrome; osteoarthritis; substance abuse including nicotine and cocaine addiction; narcolepsy; pain such as neuropathic pain, diabetic neuropathy, and chronic pain; migraines; cerebral function disorders; chronic disorders such as premenstrual syndrome; and incontinence.

This invention further encompasses pharmaceutical compositions and dosage forms which can be used, for example, in the methods disclosed herein. Preferred pharmaceutical compositions of the invention comprise a therapeutically or prophylactically effective amount of a sibutramine metabolite and optionally an additional pharmacologically active compound.

DEFINITIONS

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of desmethylsibutramine and didesmethylsibutramine that comprise biohydrolyzable moieties such as biohydrolyzable amides, biohydrolyzable esters, biohydrolyzable carbamates, biohydrolyzable carbonates, biohydrolyzable ureides, and biohydrolyzable phosphates. As used herein, prodrugs of didesmethylsibutramine do not include desmethylsibutramine and sibutramine, and prodrugs of desmethylsibutramine do not include sibutramine.

As used herein, the terms "biohydrolyzable carbamate," "biohydrolyzable carbonate," "biohydrolyzable ureide," "biohydrolyzable phosphate" mean a carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, the term "biohydrolyzable ureide" means a ureide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound.

As used herein, the term "biohydrolyzable phosphate" means a phosphate of a compound that either: 1) does not interfere with the biological activity of the compound but can confer upon that compound advantageous properties in vivo, such as uptake, duration of action, or onset of action; or 2) is biologically inactive but is converted in vivo to the biologically active compound.

As used herein, the term "pharmaceutically acceptable salt" refers to a salt prepared from a pharmaceutically acceptable non-toxic inorganic or organic acid. Inorganic acids include, but are not limited to, hydrochloric, hydrobromic, hydroiodic, nitric, sulfuric, and phosphoric. Organic acids include, but are not limited to, aliphatic, aromatic, carboxylic, and sulfonic organic acids including, but not limited to, formic, acetic, propionic, succinic, benzoic camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, alginic, and galacturonic acid.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, the terms "optically pure," "enantiomerically pure," "pure enantiomer," and "optically pure enantiomer" mean a composition that comprises one enantiomer of a compound and is substantially free of the opposite enantiomer of the compound. A typical optically pure compound comprises greater than about 80% by weight of one enantiomer of the compound and less than about 20% by weight of the opposite enantiomer of the compound, more preferably greater than about 90% by weight of one enantiomer of the compound and less than about 10% by weight of the opposite enantiomer of the compound, even more preferably greater than about 95% by weight of one enantiomer of the compound and less than about 5% by weight of the opposite enantiomer of the compound, and most preferably greater than about 97% by weight of one enantiomer of the compound and less than about 3% by weight of the opposite enantiomer of the compound. For example, optically pure (R) sibutramine comprises at least about 80% by weight (R) sibutramine and less than about 20% by weight (S) sibutramine.

As used herein, the term "neuronal monoamine reuptake inhibitor" means a substance that inhibits the reuptake of neuronal monoamines such as dopamine, serotonin, and norepinephrine as determined using in vitro assays known to those skilled in the art. Preferred neuronal monoamine reuptake inhibitors are dopamine reuptake inhibitors, and sibutramine metabolites in particular. More preferred neuronal monoamine reuptake inhibitors are optically pure sibutramine metabolites.

As used herein, the term "dopamine reuptake inhibitor" means a substance that inhibits the reuptake of dopamine as determined using in vitro assays known to those skilled in the art. Preferred dopamine reuptake inhibitors are sibutramine metabolites and apomorphine.

As used herein, the term "sibutramine metabolite" encompasses, but is not limited to, racemic and optically pure desmethylsibutramine and didesmethylsibutramine, i.e., (R)-desmethylsibutramine, (S)-desmethylsibutramine, (R/S)-desmethylsibutramine, (R)-didesmethylsibutramine, (S)-didesmethylsibutramine, and (R/S)-didesmethylsibutramine. Preferred sibutramine metabolites are optically pure.

It should further be noted that names used herein to identify compounds of the invention may differ from those that are concordant with International Union of Pure and Applied Chemistry (IUPAC) naming conventions. If there is a discrepancy between a structure depicted herein and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

DETAILED DESCRIPTION OF THE INVENTION

This invention relates, in part, to methods of treating and preventing disorders and conditions in patients (e.g., mammals such as humans, dogs, cats, and feedstock) that are ameliorated by the inhibition of the reuptake of neuronal monoamines (e.g., dopamine, serotonin, and norepinephrine). The invention further relates to pharmaceutical compositions and dosage forms that can be used in such methods.

Specific disorder and conditions that are ameliorated by the inhibition of neuronal monoamine uptake include, but are not limited to: eating disorders such as weight gain and obesity; platelet adhesion; apnea; obsessive-compulsive disorders; affective disorders (e.g., ADHD), depression, or anxiety; male and female sexual function disorders, such as erectile dysfunction; restless leg syndrome; osteoarthritis; irritable bowel syndrome; substance abuse including, nicotine addiction from cigarette smoking or chewing tobacco, and cocaine addiction; migraines; chronic pain; pain, such as neuropathic pain, such as diabetic neuropathy; cerebral function disorders; chronic disorders; and incontinence.

Methods of the invention comprise administering to a patient in need of treatment or prevention a therapeutically or prophylactically effective amount of neuronal monoamine reuptake inhibitor. Preferred neuronal monoamine reuptake inhibitors are dopamine reuptake inhibitors, such as sibutramine metabolites and pharmaceutically acceptable salts, solvates, clathrates, and prodrugs thereof. Preferred sibutramine metabolites are optically pure. Specific preferred sibutramine metabolites are (R)-desmethylsibutramine and (R)-didesmethylsibutramine. Another preferred dopamine reuptake inhibitor is apomorphine.

A first embodiment of the invention encompasses a method of treating or preventing a sexual function disorder in a patient in need of such treatment or prevention, which comprises administering to a patient in need of such treatment or prevention a therapeutically or prophylactically effective amount of a dopamine reuptake inhibitor, optionally in combination with a 5-HT$_3$ antagonist. In one method of this embodiment, a sibutramine metabolite is administered in combination with a 5-HT$_3$ antagonist. In another method of this embodiment, apomorphine is administered in combination with a 5-HT$_3$ antagonist.

In a preferred method of this embodiment, a sibutramine metabolite, or a pharmaceutically acceptable salt, solvate, hydrate, clathrate, or prodrug thereof, is administered to a patient orally, transdermally, or mucosally.

In another preferred method of this embodiment, the patient in need of treatment or prevention is elderly or postmenstrual.

As used herein, the terms "sexual dysfunction" and "sexual function disorder" encompass sexual dysfunction in men and women caused by psychological and/or physiological factors. Examples of sexual dysfunction include, but are not limited to, erectile dysfunction, vaginal dryness, lack of sexual excitement, or inability to obtain orgasm. The term "sexual dysfunction" further encompasses psycho-sexual dysfunction. Examples of psycho-sexual dysfunction include, but are not limited to, inhibited sexual desire, inhibited sexual excitement, inhibited female orgasm, inhibited male orgasm, premature ejaculation, functional dyspareunia, functional vaginismus, and atypical psycho-sexual dysfunction.

Another embodiment of the invention encompasses a method of treating or preventing an affective disorder which comprises administering to a patient in need of such treatment or prevention a therapeutically or prophylactically effective amount of a sibutramine metabolite, or a pharmaceutically acceptable salt, solvate, hydrate, clathrate, or prodrug thereof.

Affective disorders include, but are not limited to, depression (e.g., melancholia), attention deficit disorder (including attention deficit disorder with hyperactivity and attention deficit/hyperactivity disorder), bipolar and manic conditions, dysthymic disorder, and cyclothymic disorder. As used herein, the terms "attention deficit disorder" (ADD), "attention deficit disorder with hyperactivity" (ADDH), and "attention deficit/hyperactivity disorder" (AD/HD), are used in accordance with their accepted meanings in the art. See, e.g., *Diagnostic and Statistical Manual of Mental Disorders*, Fourth Ed., American Psychiatric Association, 1997 (DSM-IV™) and *Diagnostic and Statistical Manual of Mental Disorders*, 3$^{rd}$ Ed., American Psychiatric Association (1981) (DSM-III™).

A preferred method of this embodiment is a method of treating or preventing attention deficit disorder which comprises administering to a patient in need of such treatment or prevention a therapeutically or prophylactically effective amount of sibutramine metabolite, or a pharmaceutically acceptable salt, solvate, hydrate, clathrate, or prodrug thereof. In a particular embodiment, the method can also be used to treat or prevent a condition in children (e.g., ages 3–18).

Another preferred method of this embodiment is a method of treating or preventing depression which comprises administering to a patient in need of such treatment or prevention a therapeutically or prophylactically effective amount of a sibutramine metabolite, or a pharmaceutically acceptable salt, solvate, hydrate, clathrate, or prodrug thereof.

As used herein, the term "treating or preventing depression" means relief from or prevention of the symptoms of depression which include, but are not limited to, changes in mood, feelings of intense sadness, despair, mental slowing, loss of concentration, pessimistic worry, agitation, and self-deprecation. Physical changes can also be relieved or prevented by this method, and include, but are not limited to, insomnia, anorexia, decreased energy and libido, and abnormal hormonal circadian rhythms.

Another embodiment of the invention encompasses a method of treating or preventing weight gain or obesity which comprises administering to a patient in need of such treatment or prevention a therapeutically or prophylactically effective amount of a sibutramine metabolite, or a pharmaceutically acceptable salt, solvate, hydrate, clathrate, or prodrug thereof, optionally in combination with a lipase inhibitor.

As used herein, the term "treating or preventing weight gain or obesity" means reduction of weight, relief from being overweight, treating weight gain caused by the administration of other drugs, relief from gaining weight, or relief from obesity, and prevention from gaining weight, all of which are usually due to unnecessary consumption of food. The invention also encompasses methods of treating or preventing conditions incidental to obesity including, but not limited to, hypertension, such as pulmonary hypertension; cancers, such as breast, colon, gall bladder, and endometrial; gall stones; cardiovascular disease, such as dyslipidemia and carotid intimal medial thickening; hiatial hernia; osteoarthritis; gout; thyroid disease, such as diabetes; gastro-esophogeal reflux disease; menstrual dysfunction; and infertility.

Another embodiment encompasses a method of treating or preventing a disorder associated with the administration of a lipase inhibitor for obesity or weight management, such as, for example, orlistat (XENICAL®), which comprises administering to a patient in need of such treatment or prevention a therapeutically or prophylactically effective amount of a sibutramine metabolite, or a pharmaceutically acceptable salt, solvate, hydrate, clathrate, or prodrug thereof. As used herein, the term "treating or preventing a disorder associated with the administration of a lipase inhibitor" means alleviating or reducing adverse effects associated with administration of a lipase inhibitor, which include, but are not limited to, infectious diarrhea, oily fecal spotting, flatus with discharge, fecal urgency, fatty/oily stool, oily evacuation, increased defecation, anal leakage, and fecal incontinence.

Another embodiment encompasses a method of treating or preventing a cerebral function disorder which comprises administering to a patient in need of such treatment or prevention a therapeutically or prophylactically effective amount of a sibutramine metabolite, or a pharmaceutically acceptable salt, solvate, hydrate, or clathrate thereof.

Cerebral function disorders include, but are not limited to, senile dementia, Alzheimer's type dementia, memory loss, amnesia/amnestic syndrome, disturbance of consciousness, coma, lowering of attention, speech disorders, Parkinson's disease, Lennox syndrome, autism, epilepsy, hyperkinetic syndrome, and schizophrenia. Cerebral function disorders can be induced by factors including, but not limited to, cerebrovascular diseases, such as cerebral infarction, cerebral bleeding, cerebral arteriosclerosis, cerebral venous thrombosis, and head injuries, and conditions having symptoms selected from the group consisting of disturbances of consciousness, senile dementia, coma, lowering of attention, and speech disorders. As used herein, the term "treating or preventing a cerebral function disorder" means relief from or prevention of one or more symptoms associated with cerebral function disorders.

Another embodiment encompasses a method of treating or preventing restless leg syndrome, which comprises administering to a patient in need of such treatment or prevention a therapeutically or prophylactically effective amount of a sibutramine metabolite, or a pharmaceutically acceptable salt, solvate, hydrate, clathrate, or prodrug thereof.

In a preferred embodiment, the patient is at least about 50, 60, or 70 years of age. In another preferred method of this embodiment, the sibutramine metabolite is administered in combination with at least one of pergolide, carbidopa, levodopa, oxycodone, carbamazepine, gabapentin, or pharmaceutically acceptable salts, solvates, hydrates, clathrates, prodrugs, optically and pharmacologically active stereoisomers, or pharmacologically active metabolites thereof.

As used herein, the term "restless leg syndrome" encompasses a disorder that typically occurs during sleep or rest, or just before sleep or rest, and which is characterized by uncomfortable sensations in the legs. The disorder often occurs in patients older than about 50 years of age. Examples of uncomfortable sensations in the legs include, but are not limited to, pulling, drawing, crawling, wormy, boring, tingling, pins and needles, prickly and sometimes painful sensations that are usually accompanied by an overwhelming urge to move the legs. As used herein, the term "restless leg syndrome" also encompasses Ekbom Syndrome, Wittmaack-Ecbom Syndrome, Hereditary Acromelalgia, and Anxieties Tibialis.

Another embodiment encompasses a method of treating or preventing pain which comprises administering to a patient in need of such treatment or prevention a therapeutically or prophylactically effective amount of a sibutramine metabolite, or a pharmaceutically acceptable salt, solvate, hydrate, clathrate, or prodrug thereof. In a particular embodiment, the pain is chronic pain, such as neuropathic pain and diabetic neuropathy.

Still another embodiment of the invention encompasses a method of treating or preventing obsessive-compulsive disorder which comprises administering to a patient in need of such treatment or prevention a therapeutically or prophylactically effective amount of a sibutramine metabolite, or a pharmaceutically acceptable salt, solvate, hydrate, clathrate, or prodrug thereof.

As used herein, the terms "obsessive-compulsive disorder," "pre-menstrual syndrome," "anxiety," and "eating disorder" are used consistently with their accepted meanings in the art. See, e.g., DSM-IV™ and DSM-III™. The term "methods of treating or preventing" when used in connection with these disorders means the amelioration, prevention, or relief from symptoms and/or effects associated with these disorders.

Another embodiment encompasses a method of treating or preventing substance abuse which comprises administering to a patient in need of such treatment or prevention a therapeutically or prophylactically effective amount of a sibutramine metabolite, or a pharmaceutically acceptable salt, solvate, hydrate, clathrate, or prodrug thereof. In a particular embodiment, the substance abuse is cocaine addiction or alcohol addiction.

As used herein, the term "substance abuse" encompasses the abuse of, and physical and/or psychological addiction to, drugs or alcohol. The term "substance abuse" further encompasses its accepted meaning in the art. See, e.g., DSM-IV™ and DSM-II™. A preferred method encompassed by this embodiment is a method of treating or preventing cocaine and/or heroin abuse.

Another embodiment encompasses a method of treating or preventing nicotine addiction which comprises administering to a patient in need of such treatment or prevention a therapeutically or prophylactically effective amount of a sibutramine metabolite, or a pharmaceutically acceptable salt, solvate, hydrate, clathrate, or prodrug thereof. Nicotine addiction includes nicotine addiction of all known forms, such as addiction to cigarettes, cigars and/or pipes, and chewing tobacco.

Another embodiment encompasses a method of eliciting smoking cessation which comprises administering to a patient who smokes tobacco a therapeutically effective amount of a sibutramine metabolite, or a pharmaceutically acceptable salt, solvate, hydrate, clathrate, or prodrug thereof. In a preferred method encompassed by this embodiment, the sibutramine metabolite, or pharmaceutically acceptable salt, solvate, hydrate, clathrate, or prodrug thereof is administered orally, mucosally, or transdermally. In a more preferred method, the sibutramine metabolite or pharmaceutically acceptable salt, solvate, hydrate, or clathrate thereof is administered transdermally.

In another preferred method of this embodiment, the sibutramine metabolite or pharmaceutically acceptable salt, solvate, hydrate, clathrate, or prodrug thereof, is administered in combination with a therapeutically or prophylactically effective amount of nicotine. Preferably, the nicotine and/or sibutramine metabolite or pharmaceutically acceptable salt, solvate, hydrate, clathrate, or prodrug thereof is administered orally, mucosally, or transdermally. More preferably, the nicotine and/or sibutramine metabolite or pharmaceutically acceptable salt, solvate, ester, clathrate, or prodrug thereof is administered transdermally.

Another method encompassed by this embodiment is a method of treating or preventing weight gain associated with smoking cessation which comprises administering to a patient in need of such treatment or prevention a therapeutically or prophylactically effective amount of a sibutramine metabolite, or a pharmaceutically acceptable salt, solvate, hydrate, clathrate, or prodrug thereof.

Another embodiment encompasses a method of treating or preventing weight gain associated with the administration of other drugs that may induce weight gain, which comprises administering to a patient in need of such treatment or prevention a therapeutically or prophylactically effective amount of a sibutramine metabolite, or a pharmaceutically acceptable salt, solvate, ester, clathrate, or prodrug thereof.

Another embodiment encompasses a method of treating or preventing a chronic disorder including, but not limited to, narcolepsy, chronic fatigue syndrome, seasonal affective disorder, fibromyalgia, and premenstrual syndrome (or premenstrual dysphoric disorder), which comprises administering to a patient in need of such treatment or prevention a therapeutically or prophylactically effective amount of a sibutramine metabolite, or a pharmaceutically acceptable salt, solvate, hydrate, clathrate, or prodrug thereof. Preferred methods are methods of treating or preventing narcolepsy, premenstrual syndrome, or chronic fatigue syndrome.

Another embodiment encompasses a method of treating or preventing anxiety which comprises administering to a patient in need of such treatment or prevention a therapeutically or prophylactically effective amount of a sibutramine metabolite, or a pharmaceutically acceptable salt, solvate, hydrate, clathrate, or prodrug thereof.

Another embodiment encompasses a method of treating or preventing an eating disorder including, but not limited to, anorexia, bulimia, binging, and snacking, which comprises administering to a patient in need of such treatment or prevention a therapeutically or prophylactically effective amount of a sibutramine metabolite, or a pharmaceutically acceptable salt, solvate, hydrate, clathrate, or prodrug thereof.

Another embodiment encompasses a method of treating or preventing migraines which comprises administering to a patient in need of such treatment or prevention a therapeutically or prophylactically effective amount of a sibutramine metabolite, or a pharmaceutically acceptable salt, solvate, hydrate, clathrate, or prodrug thereof.

Another embodiment encompasses a method of treating or preventing incontinence which comprises administering to a patient in need of such treatment or prevention a therapeutically or prophylactically effective amount of a sibutramine metabolite, or a pharmaceutically acceptable salt, solvate, ester, clathrate, or prodrug thereof. In particular, the sibutramine metabolite can be used to treat fecal incontinence, stress urinary incontinence ("SUI"), urinary exertional incontinence, urge incontinence, reflex incontinence, passive incontinence, anal leakage, and overflow incontinence.

As used herein, the term "treating or preventing incontinence" means treatment, prevention of, or relief from the symptoms of incontinence including involuntary voiding of feces or urine, and dribbling or leakage or feces or urine, which may be due to one or more causes including, but not limited to, pathology altering sphincter control, loss of cognitive function, overdistention of the bladder, hyperreflexia and/or involuntary urethral relaxation, weakness of the muscles associated with the bladder or neurologic abnormalities.

A preferred method encompassed by this embodiment is a method of treating or preventing stress urinary incontinence. In a further preferred method encompassed by this embodiment, the patient is an elder human of an age greater than about 50 or a child of an age less than about 13.

In a specific embodiment of each of the methods of treatment or prevention of the invention, a therapeutically or prophylactically effective amount of a racemic or optically pure sibutramine metabolite is administered to a patient in combination with an additional pharmacologically active compound. Examples of additional pharmacologically active compounds include, but are not limited to, drugs that act on the central nervous system ("CNS"), such as, but not limited to: 5-HT (e.g., 5-HT$_3$ and 5-HT$_{1A}$) agonists and antagonists; selective serotonin reuptake inhibitors ("SSRIs"); hypnotics and sedatives; drugs useful in treating psychiatric disorders including antipsychotic and neuroleptic drugs, antianxiety drugs, antidepressants, and mood-stabilizers; CNS stimulants such as amphetamines; dopamine receptor agonists; antimonic agents; antipanic agents; cardiovascular agents (e.g., beta blockers and angiotensin converting enzyme inhibitors); phosphodiesterase inhibitors; antivirals; antibiotics; antifungals; and antineoplastics. As discussed in more detail herein, the particular additional pharmacologically active compound used in a method will depend upon the disease or condition being treated or prevented, as well as the particular patient being treated.

The invention also encompasses pharmaceutical compositions and single unit dosage forms that can be used, for example, in the methods described herein. One embodiment of the invention encompasses a pharmaceutical composition or dosage form that comprises a sibutramine metabolite, preferably an optically pure sibutramine metabolite. Particular pharmaceutical compositions and single unit dosage forms of the invention comprise a sibutramine metabolite and an additional pharmacologically active compound.

SYNTHESIS OF SIBUTRAMINE METABOLITES

Racemic sibutramine, desmethylsibutramine, and didesmethylsibutramine can be prepared by methods known to those of ordinary skill in the art. See, e.g., U.S. Pat. No. 4,806,570, which is incorporated herein by reference; J.

*Med. Chem.*, 2540 (1993) (tosylation and azide replacement); Butler, D., *J. Org. Chem.*, 36:1308 (1971) (cycloalkylation in DMSO); *Tetrahedron Lett.*, 155–58 (1980) (Grignard addition to nitrile in benzene); *Tetrahedron Lett.*, 857 (1997) (OH to azide); and Jeffery, J. E., et al., *J. Chem. Soc. Perkin. Trans* 1, 2583 (1996). A preferred method of preparing racemic sibutramine is provided below in Example 1.

Racemic sibutramine, desmethylsibutramine, and didesmethylsibutramine can be prepared from each other, as can optically pure forms of the compounds. Preferred methods of preparing compounds from one another are provided below in Examples 2, 3, and 8. Optically pure enantiomers of sibutramine and its metabolites can be prepared using techniques known in the art. A preferred technique is resolution by fractional crystallization of diastereomeric salts formed with optically active resolving agents. See, e.g., "Enantiomers, Racemates and Resolutions," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, New York, 1962); and S. H. Wilen *Tables of Resolving Agents and Optical Resolutions* 268 (E. L. Eliel ed., Univ. of Notre Dame Press, Notre Dame, Ind., 1972).

Because sibutramine, desmethylsibutramine, and didesmethylsibutramine are basic amines, diastereomeric salts of these compounds that are suitable for separation by fractional crystallization are readily formed by addition of optically pure chiral acid resolving agents. Suitable resolving agents include, but are not limited to, optically pure tartaric, camphorsulfonic acid, mandelic acid, and derivatives thereof. Optically pure isomers of sibutramine, desmethylsibutramine, and didesmethylsibutramine can be recovered either from the crystallized diastereomer or from the mother liquor, depending on the solubility properties of the particular acid resolving agent employed and the particular acid enantiomer used. The identity and optical purity of the particular sibutramine or sibutramine metabolite isomer so recovered can be determined by polarimetry or other analytical methods.

Racemic and optically pure sibutramine metabolites are preferably synthesized directly by methods such as those disclosed by Jeffery, J. E., et al., *J. Chem. Soc. Perkin. Trans* 1, 2583 (1996). A preferred method of directly synthesizing racemic desmethylsibutramine comprises the reduction of cyclobutanecarbonitrile (CCBC) to form an aldehyde intermediate which is subsequently reacted with an amine such as, but not limited to, methylamine. This method is applied below in Example 4.

Another preferred method of directly synthesizing racemic desmethylsibutramine comprises the reaction of CCBC with a compound of formula i-BuMX, wherein X is Br or I and M is selected from the group consisting of Li, Mg, Zn, Cr, and Mn. Preferably, the compound is of the formula i-BuMgBr. This reaction produces a product which is subsequently reduced, converted to an intermediate comprising an aldehyde bound to the nitrogen atom, which intermediate is finally converted to desmethylsibutramine in a step that comprises the addition of a lewis acid. Preferred lewis acids are selected from the group consisting of $BH_3$·THF, $BF_3$·THF, $La(O-i-Pr)_3$, $Zr(O-i-Pr)_4$, $Ti(O-i-Pr)_2Cl_2$, $SnCl_4$, and $MgBr_2$·$OEt_2$. A most preferred lewis acid is $BH_3$·THF. This method is applied below in Example 5.

The enantiomers of desmethylsibutramine can be resolved by the formation of chiral salts as described above. Preferred chiral acids used to form the chiral salts include, but are not limited to, tartaric and mandelic acids. If tartaric acid is used, preferred solvent systems include, but are not limited to, ethanol/water and isopropyl alchol/water. If mandelic acid is used, a preferred solvent system is ethyl acetate/hexane. The resolution of desmethylsibutramine is shown below in Examples 6 and 7.

A preferred method of directly synthesizing racemic didesmethylsibutramine comprises the reaction of CCBC with a compound of formula i-BuMX, wherein X is Br or I and M is selected from the group consisting of Li, Mg, Zn, Cr, and Mn. Preferably, the compound is of the formula i-BuMgBr. The product of this reaction is then reduced under suitable reaction conditions. Application of this method is shown below in Example 9.

The enantiomers of didesmethylsibutramine can be resolved by the formation of chiral salts, as described above. Preferred chiral acids used to form the chiral salts include, but are not limited to, tartaric acid. Preferred solvent systems include, but are not limited to, acetonitrile/water/methanol and acetonitrile/methanol. The resolution of didesmethylsibutramine is shown below in Examples 11 and 12.

METHODS OF TREATMENT AND PREVENTION

In each of the methods of the invention, a therapeutically or prophylactically effective amount of a sibutramine metabolite, or a pharmaceutically acceptable salt, solvate, hydrate, clathrate, or prodrug thereof, is administered to a patient. Preferred sibutramine metabolites are optically pure.

In specific methods of the invention, the sibutramine metabolite, or pharmaceutically acceptable salt, solvate, hydrate, clathrate, or prodrug thereof, is administered to a patient in an amount from about 0.1 mg to about 60 mg, preferably from about 2 mg to about 30 mg, and more preferably from about 5 mg to about 15 mg. Such amounts can be administered daily as needed for the treatment of acute and chronic diseases and conditions.

Optionally, the sibutramine metabolite is adjunctively administered (i.e., administered in combination) with one or more additional pharmacologically active compounds. In other words, a sibutramine metabolite and an additional pharmacologically active compound can be administered to a patient as a combination, concurrently but separately, or sequentially by any suitable route. Suitable routes of administration include oral, mucosal (e.g., nasal, sublingual, buccal, rectal, and vaginal), parenteral (e.g., intravenous, intramuscular or subcutaneous), and transdermal routes.

As physicians and those skilled in the art of pharmacology will readily appreciate, the particular additional pharmacologically active compounds that can be administered in combination with a sibutramine metabolite will depend on the particular disease or condition being treated or prevented, and may also depend on the age and health of the patient to which the compounds are to be administered.

Additional pharmacologically active compounds that can be used in the methods and compositions of the invention include, but are not limited to, drugs that act on the central nervous system ("CNS"), such as, but not limited to: 5-HT (e.g., 5-$HT_3$ and 5-$HT_{1A}$) agonists and antagonists; selective serotonin reuptake inhibitors ("SSRIs"); hypnotics and sedatives; drugs useful in treating psychiatric disorders including antipsychotic and neuroleptic drugs, antianxiety drugs, antidepressants, and mood-stabilizers; CNS stimulants such as amphetamines; dopamine receptor agonists; antimonic agents; antipanic agents; cardiovascular agents (e.g., beta blockers and angiotensin converting enzyme inhibitors); phosphodiesterase inhibitors; antivirals; antibiotics; antifungals; and antineoplastics.

More specific drugs that act on the CNS include, but are not limited to, SSRIs, benzodiazepine compounds, tricyclic antidepressants, antipsychotic agents, anti-anxiolytic agents, β-adrenergic antagonists, 5-$HT_{1A}$ receptor antagonists, and 5-$HT_3$ receptor agonists. Even more specific drugs that act on the CNS include, but are not limited to, lorazepam, tomoxetine, olanzapine, respiradone, buspirone, hydroxyzine, and valium.

Examples of 5-$HT_3$ antagonists that can be used in compositions and methods of the invention include, but are not limited to, granisetron (KYTRIL®), metoclopramide (REGLAN®), ondansetron (ZOFRAN®), renzapride, zacopride, tropisetron, and optically active stereoisomers, active metabolites, and pharmaceutically acceptable salts, solvates, hydrates, clathrates, prodrugs, optically and pharmacologically active stereoisomers, and pharmacologically active metabolites thereof. Preferred 5-$HT_3$ antagonists are antiemetic agents.

Selective serotonin reuptake inhibitors are compounds that inhibit the central nervous system uptake of serotonin while having reduced or limited affinity for other neurologically active receptors. Examples of SSRIs include, but are not limited to, citalopram (CELEXA®); fluoxetine (PROZAC®) fluvoxamine (LUVOX®); paroxetine (PAXIL®); sertraline (ZOLOFT®); venlafaxine (EFFEXOR®); and pharmaceutically acceptable salts, solvates, hydrates, clathrates, prodrugs, optically and pharmacologically active stereoisomers, and pharmacologically active metabolites thereof.

Disorders that can be treated or prevented using a sibutramine metabolite, or a pharmaceutically acceptable salt, solvate, hydrate, clathrate, or prodrug thereof, in combination with an SSRIs include, but are not limited to, depression, affective disorders, anxiety, eating disorders, and cerebral function disorders such as those described herein.

Benzodiazepine compounds that can be used in the methods and compositions of the invention include, but are not limited to, those described in *Goodman & Gilman, The Pharmacological Basis of Therapeutics*, 362–373 (9$^{th}$ ed. McGraw-Hill, 1996). Examples of specific benzodiazepines include, but are not limited to, alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam, pharmacologically active metabolites and stereoisomers thereof, and pharmaceutically acceptable salts, solvates, hydrates, esters, clathrates, and prodrugs thereof. The tradenames of some of these compounds are provided below.

The clinician, physician, or psychiatrist will appreciate which of the above compounds can be used in combination with a sibutramine metabolite, or a pharmaceutically acceptable salt, solvate, hydrate, clathrate, or prodrug thereof, for the treatment or prevention of a given disorder, although preferred combinations are disclosed herein.

Disorders that can be treated or prevented using a sibutramine metabolite, or a pharmaceutically acceptable salt, solvate, hydrate, clathrate, or prodrug thereof, in combination with a benzodiazepine such as those listed above include, but are not limited to, depression, affective disorders, anxiety, eating disorders, and cerebral function disorders such as those described herein.

The invention further encompasses methods of using and pharmaceutical compositions comprising sibutramine metabolite, or a pharmaceutically acceptable salt, solvate, hydrate, clathrate, or prodrug thereof, in combination with an antipsychotic agent. Antipsychotic agents are used primarily in the management of patients with psychotic or other serious psychiatric illness marked by agitation and impaired reasoning. These drugs have other properties that possibly are useful clinically, including antiemetic and antihistamine effects and the ability to potentiate analgesics, sedatives, and general anesthetics. Specific antipsychotic drugs are tricyclic antipsychotic drugs, of which there are three subtypes: phenothiazines, thioxanthenes, and other heterocyclic compounds, all of which can be used in the methods and compositions of the invention. See, e.g., *Goodman & Gilman, The Pharmacological Basis of Therapeutics*, 404 (9$^{th}$ ed. McGraw-Hill, 1996).

Specific tricyclic antipsychotic compounds include, but are not limited to, chlorpromazine, mesoridazine, thioridazine, acetophenazine, fluphenazine, perphenazine, trifluoperazine, chlorprothixene, thiothixene, clozapine, haloperidol, loxapine, molindone, pimozide, risperidone, desipramine, and pharmaceutically acceptable salts, solvates, hydrates, clathrates, prodrugs, optically and pharmacologically active stereoisomers, and pharmacologically active metabolites thereof. The tradenames of some of these compounds are provided herein.

Disorders that can be treated or prevented using a sibutramine metabolite, or a pharmaceutically acceptable salt, solvate, hydrate, clathrate, or prodrug thereof, in combination with an antipsychotic compound, and particularly a tricyclic antipsychotic compound, include, but are not limited to, affective disorders (e.g., depression), anxiety, eating disorders, and cerebral function disorders (e.g., schizophrenia) such as those described herein.

The invention further encompasses methods of using and pharmaceutical compositions comprising a sibutramine metabolite, or a pharmaceutically acceptable salt, solvate, hydrate, clathrate, or prodrug thereof, in combination with a non-benzodiazepine or non-tricyclic agents. Examples of such additional pharmacologically active compounds include, but are limited to: olanzapine, buspirone, hydroxyzine, tomoxetine, and pharmaceutically acceptable salts, solvates, hydrates, clathrates, prodrugs, optically and pharmacologically active stereoisomers, and pharmacologically active metabolites thereof.

Chlorpromazine, which is chemically named 10-(3-dimethylaminopropyl)-2-chlorphenothiazine, is sold under the tradename THORAZINE®. THORAZINE® is indicated, inter alia, for the management of manifestations of psychotic disorders. *Physician's Desk Reference®* 3101–3104 (53$^{rd}$ ed., 1999).

The besylate salt of mesoridazine, which is chemically named 10-[2(1-methyl-2-piperidyl)ethyl]-2-methylsylfinyl)-phenothiazine, is sold under the tradename SERENTIL®. SERENTIL® is indicated in the treatment of schizophrenia, behavioral problems in mental deficiency and chronic brain syndrome, alcoholism, and psychoneurotic manifestations. *Physician's Desk Reference®* 764–766 (53$^{rd}$ ed., 1999).

Perphenazine, which is chemically named 4-[3-(2-chlorophenothiazin-10-yl)propyl-1-piperazineethanol, is sold under the tradename TRILAFON®. TRILAFON® is indicated for use in the management of the manifestations of psychotic disorders and for the control of severe nausea and vomiting in adults. *Physician's Desk Reference®* 2886–2888 (53$^{rd}$ ed., 1999).

Trifluoperazine, which is chemically named 10-[3-(4-methyl-1-piperazinyl)-propyl]-2-(trifluoromethyl)-10H-phenothiazine, is sold under the tradename STELAZINE®. STELAZINE® is indicated for the management of the manifestations of psychotic disorders and for the short-term treatment of generalized non-psychotic anxiety. *Physician's Desk Reference®* 3092–3094 ($53^{rd}$ ed., 1999).

Thiothixene, which is chemically named N,N-dimethyl-9-[3-(4-methyl-1-piperazinyl)-propylidene]thioxanthene-2-sulfonamide, is sold under the tradename NAVANE®. NAVANE® is indicated in the management of manifestations of psychotic disorders. *Physician's Desk Reference®* 2396–2399 ($53^{rd}$ ed., 1999).

Clozapine, which is chemically named 8-chloro-11-(4-methyl-1-piperazinyl)5H-dibenzo[b,e][1,4]diazepine, is sold under the tradename CLOZARIL®. CLOZARIL® is indicated for the management of severely ill schizophrenic patients who fail to respond adequately to standard antipsychotic drug treatment. *Physician's Desk Reference®* 2004–2009 ($53^{rd}$ ed., 1999).

Haloperidol, which is chemically named 4-[4-(p-chlorophenyl)-4-hydroxy-piperidonol-4'-fluorobutyrophenone, is sold under the tradename HALDOL®. HALDOL® is indicated for use in the management of patients requiring prolonged parenteral antipsychotic therapy (e.g., patients with chronic schizophrenia). *Physician's Desk Reference®* 2190–2192 ($53^{rd}$ ed., 1999).

Loxapine, which is chemically named 2-chloro-11-(4-methyl-1-piperazinyl)dibenz[b,f][1–4]oxaxepine, is sold under the tradename LOXITANE®. LOXITANE® is indicated for the management of the manifestations of psychotic disorders. *Physician's Desk Reference* 3224–3225 ($53^{rd}$ ed., 1999).

Molindone, which is chemically named 3-ethyl-6,7-dihydro-2-methyl-5-(morpholinomethyl) indol-4(5H)-one hydrochloride, is sold under the tradename MOBAN®. MOBAN® is indicated for the management of the manifestations of psychotic disorders. *Physician's Desk Reference®* 978–979 ($53^{rd}$ ed., 1999).

Pimozide, which is chemically named, 1-[1-[4,4-bis(4-fluorophenyl)butyl]4-piperidinyl]-1,3-dihydro-2H-benzimidazole-2-one, is sold under the tradename ORAP®. ORAP® is indicated for the suppression of motor and phonic tics in patients with Tourette's Disorder who have failed to respond satisfactorily to standard treatment. *Physician's Desk Reference®* 1054–1056 ($53^{rd}$ ed., 1999).

Risperidone, chemically named 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one, is sold under the tradename RISPERDAL®. RISPERDAL® is indicated for the management of the manifestations of psychotic disorders. *Physician's Desk Reference®* 1432–1436 ($53^{rd}$ ed., 1999).

The hydrochloride salt of desipramine, which is chemically named 5H-Dibenz[bf] azepine-5-propanamine-10,11-dihydro-N-methyl-monohydrochloride, is sold under the tradename NORPRAMIN®. NORPRAMIN® is indicated for the treatment of depression. *Physician's Desk Reference®* 1332–1334 ($53^{rd}$ ed., 1999).

Olanzapine, which is chemically named 2-methyl-4-(4-methyl-1-piperazinyl)-10H-thieno[2,3-b][1,5]benzodiazepine, is sold under the tradename ZYPREXA®. ZYPREXA® is indicated for the management of the manifestations of psychotic disorders. *Physician's Desk Reference®* 1641–1645 ($53^{rd}$ ed., 1999).

The hydrochloride salt of buspirone, which is chemically named 8-[4-[4-(2-pyrimidinyl) -1-piperazinyl]butyl]-8-azaspiro-[4.5]decane-7,9-dione monohydrochloride, is sold under the tradename BUSPAR®. BUSPAR® is indicated for the management of anxiety disorders or the short-term relief of the symptoms of anxiety. *Physician's Desk Reference®* 823–825 ($53^{rd}$ ed., 1999).

The hydrochloride salt of hydroxyzine, which is chemically named 1 -(p-chlorobenzhydryl) 4[2-(2-hydroxyethoxy)-ethyl] piperazine dihydrochloride, is sold under the tradename ATARAX®. ATARAX® is indicated for symptomatic relief of anxiety and tension associated with psychoneurosis and as an adjunct in organic disease states in which anxiety is manifested. *Physician's Desk Reference®* 2367–2368 ($53^{rd}$ ed., 1999).

Disorders that can be treated or prevented using a racemic or optically pure sibutramine metabolite, or a pharmaceutically acceptable salt, solvate, or clathrate thereof, in combination with an antipsychotic compound, and particularly a tricyclic antipsychotic compound, include, but are not limited to, affective disorders (e.g., depression), anxiety, eating disorders, and cerebral function disorders (e.g., schizophrenia) such as those described herein.

Disorders that can be treated or prevented using a racemic or optically pure sibutramine metabolite, or a pharmaceutically acceptable salt, solvate, or clathrate thereof, in combination with a compound selected from the group consisting of lorazepam, tomoxetine, olanzapine, respiradone, buspirone, hydroxyzine, valium, pharmacologically active metabolites and stereoisomers thereof, and pharmaceutically acceptable salts, solvates, clathrates thereof include, but are not limited to, anxiety, depression, hypertension, and attention deficit disorders.

The invention further encompasses methods of using and pharmaceutical compositions comprising a racemic or optically pure sibutramine metabolite, or a pharmaceutically acceptable salt, solvate, or clathrate thereof, in combination with a 5-HT$_{1A}$ receptor antagonist and/or a β-adrenergic antagonist. Examples of 5-HT$_{1A}$ receptor antagonists and β-adrenergic antagonists that can be used in the methods and compositions of the invention include, but are limited to: alprenolol; WAY 100135; spiperone; pindolol; (S)-UH-301; penbutolol; propranolol; tertatolol; a compound of the formula I as disclosed in U.S. Pat. No. 5,552,429, which is incorporated herein by reference; and pharmaceutically acceptable salts, solvates, hydrates, clathrates, prodrugs, optically and pharmacologically active stereolsomers, and pharmacologically active metabolites thereof.

Alprenolol, which is chemically named 1-(1-methylethyl) amino-3-[2-(2-propenyl)phenoxy]-2-propanol, is described by U.S. Pat. No. 3,466,325, which is incorporated herein by reference.

WAY 100135, which is chemically named N-(t-butyl)-3-[4-(2-methoxphenyl)-piperazin-1-yl]-2-phenylpropanamide, is described by U.S. Pat. No. 4,988,814, which is incorporated herein by reference. See also, Cliffe et al., *J. Med. Chem.,* 36:1509–1510 (1993).

Spiperone, which is chemically named 8-[4-(4-fluorophenyl)-4-oxobutyl]-1-phenyl-1,3,8-triazaspiro[4,5]decan-4-one), is described by U.S. Pat. Nos. 3,155,669 and 3,155,670, both of which are incorporated herein by reference. See also, Middlmiss et al., *Neurosci. and Biobehav. Rev.,* 16:75–82 (1992).

Pindolol, which is chemically named 4-(2-hydroxy-3-isopropylaminopropoxy)-indole, is described by U.S. Pat. No. 3,471,515, which is incorporated herein by reference. See also, Dreshfield et al., *Neurochem. Res.,* 21(5):557–562 (1996).

(S)-UH-301, which is chemically named (S)-5-fluoro-8-hydroxy-2-dipropylamino-tetralin), is well known to pharmacologists and pharmaceutical chemists. See, e.g., Hillyer et al., *J. Med. Chem.*, 33:1541–44 (1990) and Moreau et al., *Brain Res. Bull.*, 29:901–04 (1992).

Penbutolol, which is chemically named (1-(t-butylamino)-2-hydroxy-3-(2-cyclopentyl-phenoxy)propane), is sold under the tradename LEVATOL®. LEVATOL® is indicated the treatment of mild to moderate arterial hypertension. *Physician's Desk Reference®* 2908–2910 (53$^{rd}$ ed., 1999).

The hydrochloride salt of propranolol, which is chemically named 1-isopropylamino-3-(1-naphthalenyloxy)-2-propanol hydrochloride, is sold under the tradename INDERAL®. INDERAL® is indicated in the management of hypertension. *Physician's Desk Reference®* 3307–3309 (53$^{rd}$ ed., 1999).

Tertatolol, chemically named 8-(3-t-butylamino-2-hydroxypropyloxy)-thiochroman, is described by U.S. Pat. No. 3,960,891, which is incorporated herein by reference.

Disorders that can be treated or prevented using a racemic or optically pure sibutramine metabolite, or a pharmaceutically acceptable salt, solvate, or clathrate thereof, in combination with a 5-HT$_{1A}$ receptor antagonist include, but are not limited to, depression, obsessive-compulsive disorders, eating disorders, hypertension, migraine, essential tremor, hypertrophic subaortic stenosis and pheochromocytoma. A specific disorder that can be treated or prevented is post-traumatic depression disorder.

Disorders that can be treated or prevented using a racemic or optically pure sibutramine metabolite, or a pharmaceutically acceptable salt, solvate, or clathrate thereof, in combination with β-adrenergic antagonist include, but are not limited to, post myocardial infarction depression.

The invention further encompasses methods of using and pharmaceutical compositions comprising a racemic or optically pure sibutramine metabolite, or a pharmaceutically acceptable salt, solvate, or clathrate thereof, in combination with a phosphodiesterase inhibitor. Examples of phosphodiesterase inhibitors that can be used in compositions and methods of the invention include, but are not limited to, those disclosed in U.S. Pat. No. 5,250,534; U.S. Pat. No. 5,719,283; U.S. Pat. No. 6,127,363; WO 94/28902; WO 97/03675; WO 98/06722, all of which are expressly incorporated herein by reference in their entirety. Preferred phosphodiesterase inhibitors are PDE5 and PDE6 inhibitors. Particular phosphodiesterase inhibitors include, but are not limited to, sildenophil (Viagra®), desmethylsildenophil, vinopocetine, milrinone, amnrinone, pimobendan, cilostamide, enoximone, peroximone, vesnarinone, rolipran, R020–1724, zaprinast, dipyridamole, and pharmaceutically acceptable salts, solvates, hydrates, clathrates, prodrugs, optically and pharmacologically active stereoisomers, and pharmacologically active metabolites thereof.

Disorders and conditions that can be treated or prevented using a sibutramine metabolite, or a pharmaceutically acceptable salt, solvate, hydrate, clathrate, or prodrug thereof, in combination with a phosphodiesterase include, but are not limited to, sexual dysfunction and cerebral function disorders. Others disorders and conditions include, but are not limited to, pain, migraines, osteoarthritis, and restless leg syndrome.

While all combinations of racemic and optically pure sibutramine metabolites and pharmaceutically acceptable salts, solvates, and clathrate thereof, and one or more of the above-described pharmacologically active compounds can be useful and valuable, certain combinations are particularly preferred. Examples of preferred combinations include those wherein a racemic or optically pure sibutramine metabolite, or a pharmaceutically acceptable salt, solvate, clathrate, or prodrug thereof, is combined with one of the following:

| | | |
|---|---|---|
| alprazolam; | mesoridazine; | tertatolol; |
| brotizolam; | thioridazine; | desipramine; |
| chlordiazepoxide; | acetophenazine; | clonidine; |
| clobazam; | fluphenazine; | olanzapine; |
| clonazepam; | perphenazine; | methylphenidate; |
| clorazepate; | trifluoperazine; | buspirone; |
| demoxepam; | chlorprothixene; | hydroxyzine; |
| diazepam; | thiothixene; | tomoxetine; |
| estazolam; | clozapine; | sildenophil; |
| flumazenil; | haloperidol; | desmethylsildenophil; |
| flurazepam; | loxapine; | vinopocetine; |
| halazepam; | molindone; | milrinone; |
| lorazepam; | pimozide; | amrinone; |
| midazolam; | risperdone; | pimobendan; |
| nitrazepam; | alprenolol; | cilostamide; |
| nordazepam; | WAY 100135; | enoximone; |
| oxazepam; | spiperone; | peroximone; |
| prazepam; | S(S)-pindolol; | vesnarinone; |
| quazepam; | R(R)-pindolol; | rolipran; |
| temazepam; | racemic pindolol; | R020-1724; |
| triazolam; | (S)-UH-301; | zaprinast; or |
| chlorpromazine; | penbutolol; | dipyridamole. |

Suitable daily dosage ranges of additional pharmacologically active compounds that can be adjunctively administered with sibutramine metabolite can be readily determined by those skilled in the art following dosages reported in the literature and recommended in the *Physician's Desk Reference®* (54$^{th}$ ed., 2000).

For example, suitable daily dosage ranges of 5-HT$_3$ antagonists can be readily determined by those skilled in the art and will vary depending on factors such as those described herein and the particular 5-HT$_3$ antagonists used. In general, the total daily dose of a 5-HT$_3$ antagonist for the treatment or prevention of a disorder described herein is from about 0.5 mg to about 500 mg, preferably from about 1 mg to about 350 mg, and more preferably from about 2 mg to about 250 mg per day.

Similarly, suitable daily dosage ranges of phosphodiesterase inhibitors can be readily determined by those skilled in the art. In general, the total daily dose of a phosphodiesterase inhibitor will be from about 0.5 mg to about 500 mg, from about 1 mg to about 350 mg, or from about 2 mg to about 250 mg.

The therapeutic or prophylactic administration of an active ingredient of the invention (e.g., sibutramine metabolites and additional pharmacologically active compounds) is preferably initiated at a lower dose and increased, if necessary, up to the recommended daily dose as either a single dose or as divided doses, depending on the global response of the patient. An example of a lower dose of sibutramine metabolite is from about 0.1 mg to about 1 mg; an example of a lower dose of 5-HT$_3$ antagonist is from about 15 mg to about 60 mg. It is further recommended that patients aged over 65 years should receive doses of sibutramine metabolite in the range of from about 0.1 mg to about 10 mg per day depending on global response. It may be necessary to use dosages outside these ranges, which will be readily determinable by one of ordinary skill in the pharmaceutical arts.

The dosage amounts and frequencies provided above are encompassed by the terms "therapeutically effective," "prophylactically effective," and "therapeutically or prophylactically effective" as used herein. When used in connection with an amount of a racemic or optically pure sibutramine metabolite, these terms further encompass an amount of racemic or optically pure sibutramine metabolite that induces fewer or less sever adverse effects than are associated with the administration of racemic sibutramine. Adverse effects associated with racemic sibutramine include, but are not limited to, significant increases in supine and standing heart rate, including tachycardia, increased blood pressure (hypertension), increased psychomotor activity, dry mouth, dental caries, constipation, hypohidrosis, blurred or blurry vision, tension, mydriasis, seizures, formation of gallstones, renal/hepatic dysfunction, fevers, arthritis, agitation, leg cramps, hypertonia, abnormal thinking, bronchitis, dyspnea, pruritus, amblyopia, menstrual disorder, ecchymosis/bleeding disorders, interstitial nephritis, and nervousness. See, e.g., *Physician's Desk Reference*® 1494–1498 (53$^{rd}$ ed., 1999). However, the induction of fewer or less severe adverse-effects is attributable to the administration of a sibutramine metabolite and the efficacy of which may be less apparent or absent with the administration of a combination therapy.

PHARMACEUTICAL COMPOSITIONS

The invention encompasses pharmaceutical compositions and single unit dosage forms comprising a sibutramine metabolite, or a pharmaceutically acceptable salt, solvate, hydrate, clathrate, or prodrug thereof. Preferred sibutramine metabolites are optically pure. Certain pharmaceutical compositions and unit dosage forms further comprise at least one additional pharmacologically active compound.

The pharmaceutical compositions and dosage forms of this invention are particularly useful in the methods herein, and may be suitable for oral, mucosal (e.g., nasal, sublingual, buccal, rectal, and vaginal), parenteral (e.g., intravenous, intramuscular or subcutaneous), or transdermal administration.

Preferred pharmaceutical compositions and dosage forms comprise a sibutramine metabolite, or a pharmaceutically acceptable salt, solvate, hydrate, clathrate, or prodrug thereof in an amount from about 0.1 mg to about 60 mg, preferably from about 2 mg to about 30 mg, and more preferably from about 5 mg to about 15 mg. Pharmaceutical compositions and dosage forms of the invention typically also comprise one or more pharmaceutically acceptable excipients or diluents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of disorder may contain larger amounts of one or more of the active ingredients it comprises than a dosage form used in the chronic treatment of the same disorder. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients, such as, desmethylsibutramine and didesmethylsibutramine and its optically active enantiomers in particular, can be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose or mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379–80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine (e.g., desmethylsibutranine and didesmethylsibutramine) are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a racemic or optically pure sibutramine metabolite, or a pharmaceutically acceptable salt, solvate, clathrate, hydrate, or prodrug thereof in an amount of from about 0.1 mg to about 60 mg, preferably in an amount of from about 2 mg to about 30 mg, and more preferably in an amount of from about 5 mg to about 15 mg.

ORAL DOSAGE FORMS

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, fillers, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The magnitude of a prophylactic or therapeutic dose of an active ingredient in the acute or chronic management of a disorder or condition will vary with the severity of the disorder or condition to be treated and the route of administration. The dose, and perhaps the dose frequency, will also vary according to age, body weight, response, and the past medical history of the patient. Suitable dosing regimens can be readily selected by those skilled in the art with due consideration of such factors.

DELAYED RELEASE DOSAGE FORMS

Active ingredients of the invention can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

PARENTERAL DOSAGE FORMS

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

TRANSDERMAL, TOPICAL, AND MUCOSAL DOSAGE FORMS

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

KITS

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a unit dosage form of a sibutramine metabolite, or a pharmaceutically acceptable prodrug, salt, solvate, hydrate, or clathrate thereof, and a unit dosage form of an additional pharmacologically active compound. Examples of additional pharmacologically active compounds are disclosed herein.

Kits of the invention can further comprise devices that are used to administer the active ingredients. Examples of such devices include, but are not limited to, syringes, drip bags, patches, and inhalers. Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The invention is further defined by reference to the following examples. It will be apparent to those skilled in the art that many modifications, both to materials and methods, can be practiced without departing from the scope of this invention.

EXAMPLES

Examples 1–2 describe the preparation of racemic and optically pure sibutramine. Examples 3–8 describe the preparation of racemic and optically pure forms of desmethylsibutramine (DMS). In each of these examples, the enantiomeric purity of DMS was determined using a Chirobiotic V analytical column (10 mm, 4.6 mm×25 mm) with 20 mM ammonium acetate/IPA (65:35) as the mobile phase. The UV detector was set to a wavelength of 222 nm.

Examples 9–12 describe the preparation of racemic and optically pure forms of didesmethylsibutramine (DDMS). In each of these examples, the enantiomeric purity of DDMS was determined using an ULTRON ES-OVM analytical column (150 mm×4.6 mm) with 0.01 M $KH_2PO_4$/MeOH (70:30) as the mobile phase. The UV detector was set to a wavelength of 200 nm.

Examples 13–14 describe methods of determining binding affinities of the compounds of the invention and binding affinities measured using those methods.

Finally, Example 15 describes oral formulations comprising compounds of the invention.

EXAMPLE 1

SYNTHESIS OF SIBUTRAMINE

Synthesis of 1-(4-Chlorophenyl)cyclobutanecarbonitrile

To a suspension of NaH (17.6 g 60%, washed with hexane) in dimethylsulfoxide (150 mL) at room temperature with mechanical stirring was added over a one hour period a mixture of chlorbenzylnitrile (30.3 g) and 1,3-dibromopropane (22.3 mL, 44.5 g). The reaction mixture was stirred for an additional 1 hour, and isopropyl alcohol (10 mL) was added slowly to quench excess NaH. Water (150 mL) was added. The reaction mixture was extracted with t-butyl methyl ether (MTBE) (2×200 mL), and the combined extracts were washed with water (3×200 mL), brine, and dried over $MgSO_4$. The solvent was removed in a rotoevaporator, and the final product was purified by distillation to give the title compound (22 g, 56%) as pale yellow oil, bp 110–120° C./1.0 mm Hg. The product was characterized by $^1$H NMR.

Synthesis of 1-[1-(4-chlorophenyl)cyclobutyl]-3-methylbutylamine

A solution of isobutylmagnesium bromide (2M, 108 mL) in diethyl ether (Aldrich) was concentrated to remove most of the ether. The residue was dissolved in toluene (150 mL), followed by addition of the nitrile made above (22 g). The reaction mixture was heated to 105° C. for 17 hours. The reaction mixture was cooled to room temperature, and added to a slurry of $NaBH_4$ in isopropyl alcohol (450 mL). The reaction mixture was heated under reflux for 6 hours, cooled to room temperature and concentrated. The residue was diluted with water (350 mL), and extracted with ethyl acetate (3×200 mL). The combined extracts were washed with water (100 mL), and dried ($MgSO_4$), and concentrated to give 24.2 g crude product (83%).

Synthesis of Sibutramine Free Base

1-[1-(4-chlorophenyl)cyclobutyl]-3-methylbutylamine (21.6 g) was added to formic acid (27 mL) and aqueous formaldehyde (46 mL). The reaction mixture was heated to 85–95° C. for 18 hours and was cooled to room temperature. 30% NaOH was added until the mixture was basic (pH>11). The solution was extracted with chloroform (3×200 mL) and the extracts were combined and washed with water and brine and concentrated to give 15 g product.

Sibutramine HCl

Sibutramine free base (2.25 g) was dissolved in MTBE (20 mL) and that solution was added to 20 mL 1M HCl in diethyl ether. The reaction mixture was stirred for 30 minutes, and the solid was collected by filtration to give 1.73 g after drying. The product was characterized by $^1$H NMR.

Resolution of Sibutramine 12.3 g racemic sibutramine was dissolved in ethyl acetate (85 mL), and a solution of 21.7 g L-dibenzyltartaric acid ("L-DBTA") in ethyl acetate (85 mL) was added thereto. The reaction mixture was heated to reflux and cooled to room temperature. The white precipitate was collected (ee of salt is ca 85%). The solid was then suspended in 220 mL ethyl acetate and heated at reflux for 30 minutes. The solid was collected to give >95% ee. The salt was further crystallized in isopropyl alcohol (450 mL) to give 11.3 g of salt with >99.3% ee. (S)-Sibutramine L-DBTA (yield 76%). Free base was obtained by treatment of the salt with saturated aqueous NaHCO$_3$ and extracted with chloroform. The (S)-sibutramine HCl salt was obtained with treatment of the free base with HCl/Et$_2$O as described above. Optical rotation of the HCl salt was $[\alpha]$=3.15 (c=0.9, H$_2$O), $^1$H NMR $^{13}$C (CD$_3$OD), and M$^+$=279. The resolution mother liquor was treated with NaOH to give the partially enriched (R)-sibutramine and was then treated with D-DBTA as described above to give (R)-sibutramine-D-DBTA salt with >99.3% ee. The sibutramine enantiomers were characterized by $^1$H and $^{13}$C NMR: M$^+$=279. The material was also characterized by HPLC and Chiral HPLC.

EXAMPLE 2

SIBUTRAMINE FROM ITS METABOLITES

Racemic and optically pure sibutramine can also be prepared by methylation of desmethylsibutramine or dimethylation of didesmethylsibutramine under suitable reaction conditions. An example of this method is shown in Scheme 1.

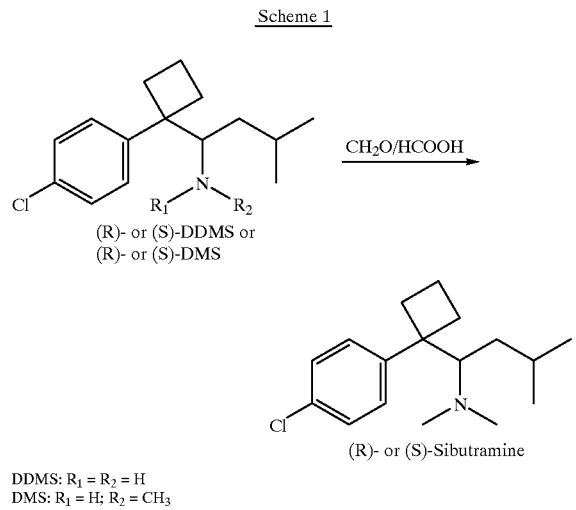

EXAMPLE 3

DESMETHYLSIBUTRAMINE FROM SIBUTRAMINE (S)-Sibutramine (1.25 g) was dissolved in toluene (90 mL) and diethylazo-dicarboxylate ("DEAD") was added (0.8 g, 1.1 eq). The reaction mixture was heated at 50° C. for 6 hours, and 0.8 g DEAD was added. The reaction was heated at 50° C. for another 6 hours, cooled to room temperature and the toluene was removed under vacuum. The residue was suspend in 45 mL of ethanol and 45 mL of saturated aqueous H$_4$Cl. The reaction mixture was heated under reflux for 3 hours. The reaction mixture was cooled to room temperature and concentrated to remove ethanol. Aqueous NaHCO$_3$ was added until the concentrate was basic. The basic concentrate was extracted with dichloromethane, (3×50 mL). The extracts were combined, dried with sodium sulfate, filtered and concentrated to give a crude product. Flash column chromatography (SiO$_2$) (ethyl acetate/TEA 99:1) gave 0.43 g product. It was characterized by $^1$H and $^{13}$C NMR, M$^+$=266, and optical rotation $[\alpha]$=−10.6, c=3.3, (CHCl$_3$.) The other enantiomer and racemate were prepared similarly and the isomer was characterized as the (S)-isomer.

Synthesis of desmethylsibutramine hydro chloride isomers

To a solution of (S)-desmethylsibutramine (0.78 g) in ethyl acetate (5 mL) at 0° C. was added HCl/diethyl ether (1 M, 5 mL). The reaction mixture was stirred for 1 hour and the solid was collected by filtration. The solid was then dried to give 0.68 g white solid. The product was characterized by $^1$H and $^{13}$C NMR (DMSO-d$_6$), and a chemical purity of >99% was determined by HPLC. $[\alpha]$=−5° (c=0.5, H$_2$O). The racemate and the other enantiomer were prepared and characterized in the same way.

EXAMPLE 4

(R/S)-DESMETHYLSIBUTRAMINE

Another method of preparing racemic desmethylsibutramine ((R/S)-DMS) is shown in Scheme 2 and described in detail below:

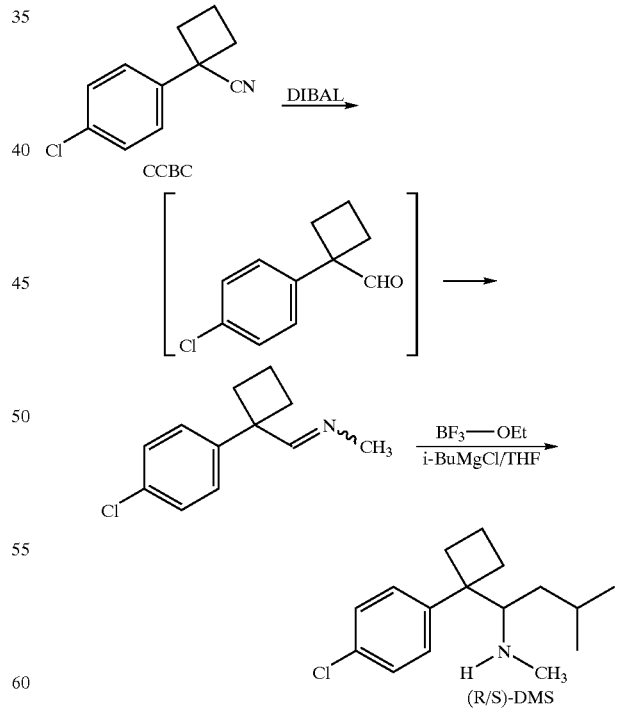

Preparation of 1-(4-Chlorophenyl)-1-cyclobutyl carboxaldehyde

Following Scheme 2, diisobutylaluminum hydride (DIBAL-H) (87 mL, 1M in THF, 87.0 mmol) was added to a solution of 1-(4-chlorophenyl) cyclobutanecarbonitrile (CCBC; 10g, 52.1 mmol) maintained at −20° C. The resulting mixture was stirred for 4–5 hours at 0° C. and then poured into a 10% aqueous citric acid solution and diluted with 200 mL MTBE. The mixture was stirred at room temperature for 3–4 hours. The aqueous layer was washed with MTBE (1×50 mL) and the combined organic layers were dried over MgSO$_4$ and concentrated to give 9 g (89%) of the above-captioned aldehyde as an oil. $^1$H NMR (CDCl$_3$) d 9.52 (s, 1H), 7.35–7.06 (m, 4H), 2.77–2.68 (m, 2H), 2.43–2.32 9m, 2H), 2.06–1.89 (m, 2H). $^{13}$C NMR d 198.9, 139.4, 132.9, 128.9, 127.8, 57.1, 28.3, 15.8.

Preparation of 1-(4-chlorophenyl)-1-cyclobutyl-N-methylcarbaimine

A mixture of 1-(4-chlorophenyl)-1-cyclobutyl carboxaldehyde (3 g, 15.4 mmol) and methyl amine (12 mL, 40% aqueous w/w, 154 mmol) was stirred at room temperature for 18–40 hours. The reaction mixture was extracted with MTBE (2×50 mL). The combined organic layers were dried over K$_2$CO$_3$ and concentrated to give 2.5 g (78%) of the above-captioned imine as an oil. $^1$H NMR (CDCl$_3$) d 7.65 (m, 1H), 7.33–7.11 (m, 4H), 3.34 (s, 3H), 2.69–2.44 (m, 2H), 2.44–2.34 (m, 2H), 2.09–1.84 (m, 2H); $^{13}$C NMR d 168.0, 144.0, 131.8, 128.4, 127.4, 50.6, 47.6, 30.6, 15.8.

Preparation of 1-(4-chlorophenyl)-N-methyl-2-(2-methylpropyl)-cyclobutanamethamine To a solution of 1-(4-chlorophenyl)-1-cyclobutyl N-methylcarbaimine (0.5 g, 2.4 mmol) cooled to 0° C. was added BF$_3$·OEt$_2$ (0.34 g, 2.4 mmol). The mixture was stirred for 1 hour and then cooled to −78° C. At this temperature, isobutyl magnesium bromide (2.5 mL, 2M in ether, 5 mmol) was added to form a mixture which was stirred at −78° C. for 2 hours and then warmed to room temperature and stirred overnight. The reaction was quenched with saturated NaHCO$_3$ solution (10 mL) and diluted with MTBE (15 mL). The organic layer was dried over MgSO$_4$, concentrated, and purified by silicagel chromatography (eluting with 1% NEt$_3$ in ethyl acetate) to give 380 mg of the above captioned amine as an oil. $^1$H NMR (CDCl$_3$) d 7.35–7.19 (m, 4H), 2.65–2.74 (m, 1H), 2.57 (s, 3H), 2.20–2.56 (m, 5H), 1.60–2.00 (m, 3H), 1.20–1.00 (m, 2H), 0.95–0.90 (m, 6H), 0.67–0.60 (m, 1H). $^{13}$C NMR δ144.7, 131.3, 129.1, 127.4, 65.5, 51.7, 41.4, 37.4, 33.7, 32.3, 25.4, 24.0, 22.0, 16.3.

EXAMPLE 5

(R/S)-DESMETHYLSIBUTRAMINE-HCL

A method of preparing the hydrochloride salt of racemic desmethylsibutramine ((R/S).DMS.HCl) is shown in Scheme 3:

Scheme 3

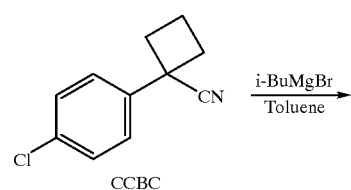

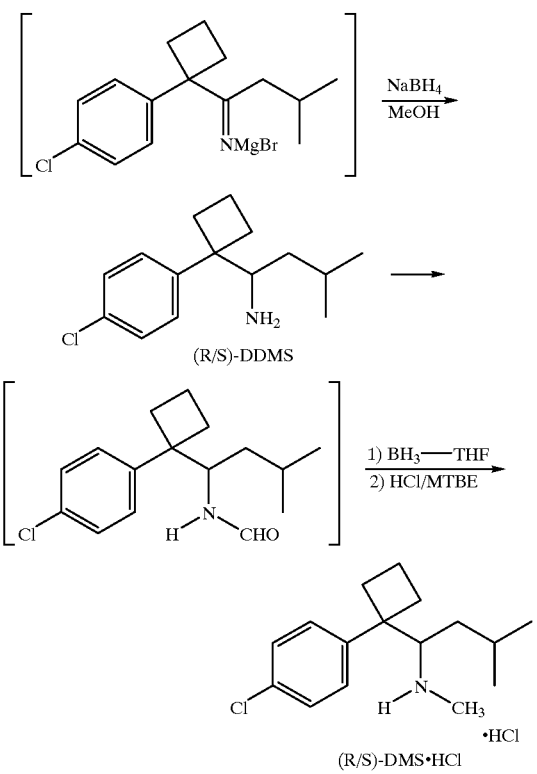

Following Scheme 3, toluene (150 mL) and a solution of CCBC (50.0 g, 261 mmol) in toluene (45 mL) were added to a solution of isobutyl magnesium bromide in THF (392 mL, 1M in THF, 392 mmol). The resulting mixture was distilled until the internal temperature reached 105–110° C. and was then refluxed at this temperature range for 2–4 hours. The reaction mixture was then cooled to 0° C. and quenched with methanol (295 mL). NaBH$_4$ (11 g, 339 mmol) was added portion-wise over 15 minutes to the reaction mixture at 0° C. After stirring for 15 minutes, the reaction mixture was transferred into a 2N aqueous HCl solution (365 mL). The organic phase was distilled until the internal temperature reached 105° C., and was then allowed to cool to room temperature. Formic acid (24 g, 522 mmol) was then added to the reaction mixture, which was then heated to reflux (92–96° C.) for 6–8 hours after which time the reaction mixture was distilled until the internal temperature reached 108° C. The mixture was then cooled to 10° C. and BH$_3$-THF (653 mL, 1.0 M, 653 mmol) was added. The resulting mixture was heated to reflux (69° C.) for 15 hours. The mixture was then cooled to 5° C., combined with methanol (105 mL), and refluxed again for 45 minutes. The reaction mixture was distilled until the internal temperature reached 116° C., and then allowed to cool to 25° C. Hydrochloric acid in MTBE (373 g, 18 wt % of HCl, 1840 mmol) was then added to the mixture to provide a white slurry which was refluxed for 1 hour and then filtered to give 62.3 g (79.0%) of (R/S)-DMS-HCl. NMR (CDCl$_3$): $^1$H ( d), 0.85–1.1 (m, 6H), 1.24–1.5 (b, 2H), 1.65–2.14 (b, 4H), 2.2–2.5 (b, 4H), 2.5–2.7 (m, 2H), 3.4–3.6 (b, 1H), 7.3–7.5 (m, 4H), 9.0–9.5 (b, 2H). $^{13}$C (d): 15.5, 21.4, 23.5, 24.7, 31.4, 32.4, 33.2, 35.9, 49.1, 64.2, 128.5, 129.4, 133.0, 141.6.

EXAMPLE 6

(R)-DESMETHYLSIBUTRAMINE-HCL

A method of preparing the hydrochloride salt of (R)-desmethylsibutramine ((R)-DMS.HCl) is shown in Scheme 4 and described in detail below:

Scheme 4

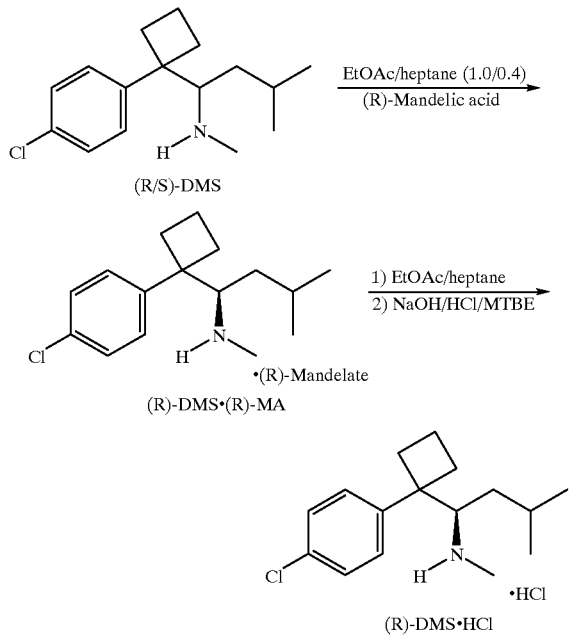

Scheme 5

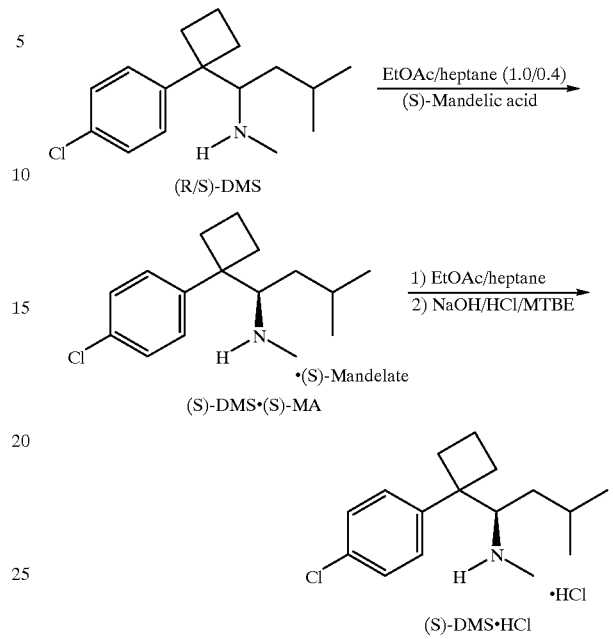

Formation of (R)-Mandelate Salt of (R)-DMS (R/S)-Desmethylsibutramine HCl ((R/S)-DMS•HCl) (60 g) was added to ethyl acetate (300 mL) and the resulting mixture was cooled to 0° C. Aqueous NaOH (1.5 N, 300 mL) was then added to the reaction mixture, which was then stirred for 30 minutes. The organic phase was separated, washed with water (150 mL), and concentrated. (R)-Mandelic acid (30.3 g), ethyl acetate (510 mL total), and heptane (204 mL) were then added to the concentrated organic phase. The resulting mixture was then heated to reflux for 1 hour, after which time it was cooled to 20–23° C. Filtration of the resulting slurry yielded 36.4 g (43.8%) of (R)-desmethylsibutramine-(R)-mandelate ((R)-DMS (R)-MA; 95.5% ee).

Enrichment of (R)-DMS (R)-MA

A mixture of (R)-DMS•(R)-MA (30 g, 0.072 mol), ethyl acetate (230 mL), and heptane (230 mL) was heated to reflux for 1 hour. After cooling to 20–23 ° C., the product was filtered and dried to give 29.6 g (98%) of (R)-DMS•(R)-MA (99.9% ee).

Formation of HCl Salt of (R)-DMS

A mixture of (R)-DMA•(R)-MA (50 g, 0.12 mol), NaOH (100 ml, 3.0 N), and toluene (500 mL) was stirred for 30 minutes. The organic phase was washed with water (200 mL), concentrated to about 300 mL, and cooled to room temperature. HCl/MTBE (100 mL, 14%, 0.34 mol) was then slowly added to the mixture to form (R)-DMA.HCl. After stirring for 30 minutes, the slurry was filtered and the resulting wet cake was washed two times with MTBE and dried to give 34.5 g (95.5%) of (R)-DMA.HCl (99.9% ee; 99.9% chemically pure by NMR). NMR (CDCl$_3$): $^1$H ( d), 0.85–1.1 (m, 6H), 1.24–1.5 (b, 2H), 1.65–2.14 (b, 4H), 2.2–2.5 (b, 4H), 2.5–2.7 (m, 2H), 3.4–3.6 (b, 1H), 7.3–7.5 (m, 4H), 9.0–9.5 (b, 2H). $^{13}$C (d): 15.5, 21.4, 23.5, 24.7, 31.4, 32.4, 33.2, 35.9, 49.1, 64.2, 128.5, 129.4, 133.0, 141.6.

EXAMPLE 7. (S)-DESMETHYLSIBUTRAMINE-HCL

A method of preparing the hydrochloride salt of (S)-desmethylsibutramine (S)-DMA.HCl) is shown in Scheme 5 and described in detail below:

Formation of (S)-Mandelate Salt of (S)-DMS

Following Scheme 5, a mixture of (R/S-DMA.HCl (5.0 g), NaOH (1.5N, 20 mL) and ethyl acetate (50 mL) was stirred for 30 minutes. The organic phase was washed with water (20 mL) and concentrated to give desmethylsibutramine free base (4.2 g, 96%).

Desmethylsibutramine free base (1.1 g, 4.1 mmol) was combined with (S)-mandelic acid (0.62 g, 4.1 mmol), ethyl acetate (11 mL), and heptane (4.4 mL). The resulting mixture was heated to reflux for 30 minutes and cooled to 20–23° C. Filtration of the resulting slurry gave 0.76 g of (S)-desmethylsibutramine•(S)-mandelate salt ((S)-DMS. (S)-MA) (96% ee).

Enrichment of (S)-DMS-(S)-MA

A mixture of (S)-Desmethylsibutramine•(S)-mandelate (0.76 g), ethyl acetate (5 mL), and heptane (5 mL) was heated to reflux for 1 hour. After cooling to 20–23 ° C., the product was filtered and dried to give 0.72 g (95%) of (S)-DMS-(S)-MA (99.9% ee).

Recovery of (S)-Mandelate Salt of (S)-DMS from Mother Liquor of (S)-DMA•(R)-MA

A solution of (S)-DMA•(R)-MA in ethyl acetate-heptane (67% ee mother liquor) was charged with NaOH (3N, 400 mL) and the reaction mixture was stirred for 30 minutes. The organic phase was washed with water and concentrated. The resulting residue (130 g, 0.49 mol and 67% ee) was charged with (S)-mandelic acid (28.5 g, 0.49 mol), ethyl acetate (1400 mL), and heptane (580 mL). The mixture was heated to reflux for 1 hour and then slowly cooled to room temperature. The resulting slurry was filtered and dried to give 147 g (86% based on (S)-isomer) of (S)-DMA•(S)-MA (99.9% ee).

Formation of HCl Salt of (S)-DMS (S)-Desmethylsibutramine•(S)-mandelate (20 g, 0.048 mol) was added to a mixture of NaOH (60ml, 3.0 N) and toluene (200 mL). The mixture was stirred for 30 minutes and the organic phase was then washed with water (100 mL), concentrated to about 100 mL, and cooled to room temperature. Hydrochloric acid in MTBE (40 mL, 14%, 0.13 mol) was then added slowly to the mixture to form (S)-DMA•HCl. After stirring for 30 minutes, the slurry was filtered and the resulting wet cake was washed two times with MTBE and dried to give 14 g (96.7%) of (S)-DMS-(L)-MA (99.9% ee; 99.9% chemical purity). NMR (CDCl$_3$): $^1$H (d), 0.84–1.1 (m, 6H), 1.25–1.5 (b, 2H), 1.65–2.15 (b, 4H), 2.2–2.5 (b, 4H), 2.5–2.7 (m, 2H), 3.4–3.6 (b, 1H), 7.3–7.5 (m, 4H), 9.0–9.5 (b, 2H). $^{13}$C (d): 15.5, 21.4, 23.5, 24.7, 31.4, 32.4, 33.2, 35.9, 49.1, 64.2, 128.5, 129.4, 133.0, 141.6.

EXAMPLE 8. DESMETHYLSIBUTRAMINE FROM DIDESMETHYLSIBUTRAMINE

Racemic and optically pure didesmethylsibutramine can also be prepared by methylation of didesmethylsibutramine under suitable reaction conditions. An example of this method is shown in Scheme 6.

Scheme 6

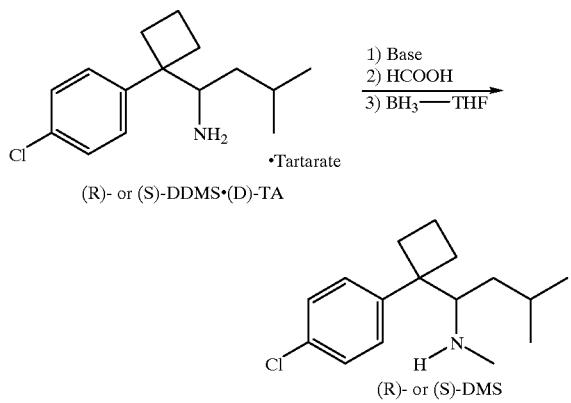

(R)- or (S)-DDMS•(D)-TA (R)- or (S)-DMS

EXAMPLE 9. (R/S)-DIDESMETHYLSIBUTRAMINE

A preferred method of preparing racemic didesmethylsibutramine free base ((R/S)-DDMS) is shown in Scheme 7 and described in detail below.

Scheme 7

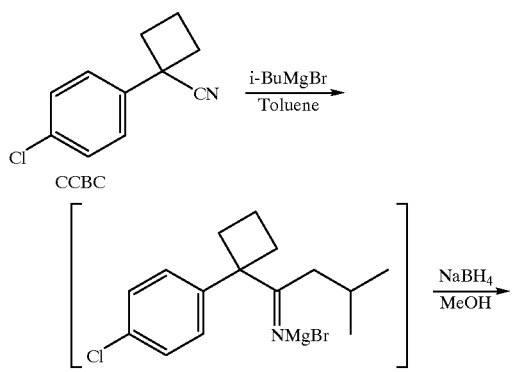

-continued

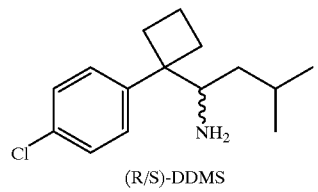

(R/S)-DDMS

Following Scheme 7, a 1 L three-necked round bottom flask was charged with isobutyl magnesium bromide (200 mL, 2.0 M in diethyl ether) and toluene (159 mL) and the resulting mixture was distilled to remove most of the ether. After the mixture was cooled to 20° C., CCBC (50.0 g) in toluene (45 mL) was added, and resulting mixture was refluxed for 2–4 hours. The reaction mixture was then cooled to 0° C. and methanol (300 mL) was added to it, followed slowly by NaBH$_4$ (11 g). The resulting mixture was then stirred at about 0–10° C. for 15 minutes. The reaction mixture was then added slowly to an aqueous HCl solution (365 mL, 2N) kept at 0° C., and the resulting mixture was warmed to room temperature with continual stirring. After separation of the organic phase, the aqueous phase was washed with toluene (200 mL). The combined organic phases were washed with water (200 mL) and concentrated to give (R/S)-DDMS (55 g, 85%). NMR (CDCl$_3$): $^1$H (d), 0.6–0.8 (m, 1H), 0.8–1.0 (m, 6H), 1.1–1.3 (m, 1H), 1.6–2.6 (m, 7H), 3.0–3.3 (m, 1H), 7.0–7.6 (m, 4H). $^{13}$C (d): 15.4, 21.5, 24.3, 24.7, 31.5, 31.9, 41.1, 50.73, 56.3, 127.7, 129, 131.6, 144.3.

EXAMPLE 10. (R/S)-DIDESMETHYLSIBUTRAMINE (D)-TARTRATE

A preferred method of preparing the (D)-tartrate salt of racemic didesmethylsibutramine ((R/S)-DDMS•(D)-TA) is shown below in Scheme 8. It should be noted that the (L)-tartrate salt of racemic didesmethylsibutramine ((R/S)-DDMA•(L)-TA) can be prepared in an analogous manner.

Scheme 8

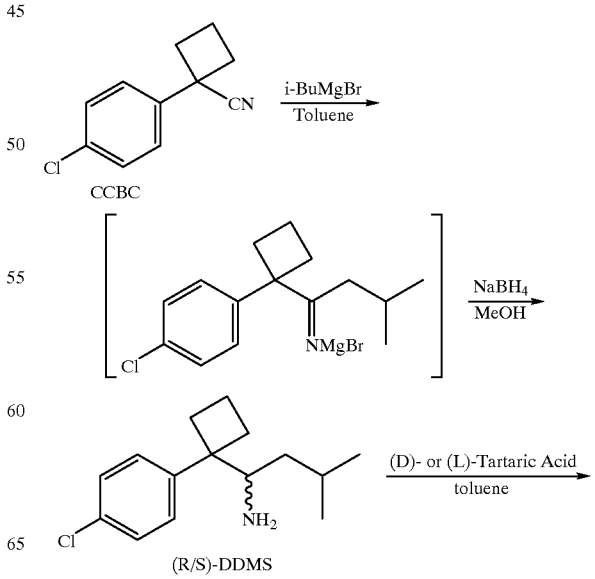

(R/S)-DDMS

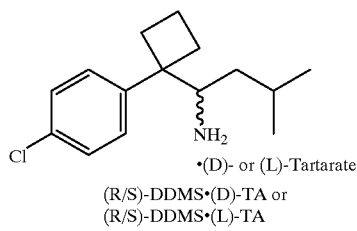

•(D)- or (L)-Tartarate (R/S)-DDMS•(D)-TA or
(R/S)-DDMS•(L)-TA

Following Scheme 8, a mixture of racemic didesmethyl-sibutramine (15.3 g) and toluene (160 mL) was heated to 70–80° C. and (D)-tartaric acid (9.1 g) in water (20 mL) and acetone (10 mL) was added slowly. The resulting mixture was refluxed for 30 minutes, after which the water and acetone were removed by distillation. The resulting mixture was cooled to room temperature to provide a slurry which was then filtered. The resulting wet cake was washed two times with MTBE (20 mL×2) and dried to yield (R/S)-DDMA•(D)-TA (22.5g, 98%). NMR (DMSO): $^1$H (d), 0.6–0.92 (m, 6H), 0.92–1.1 (m, 1H), 1.1–1.3 (m, 1H), 1.5–1.8 (m, 2H), 1.8–2.1 (m, 1H, 2.1–2.4 (m, 3H), 2.4–2.6 (m, 1H), 3.4–3.6 (m, 1H), 3.9–4.2 (s, 2H), 6.4–7.2 (b, 6H, OH, COOH and NH2), 7.3–7.6 (m, 4H). $^{13}$C (d): 15.5, 2.1, 23.3, 23.7, 31.5, 31.8, 37.7, 39.7, 54.5, 72.1, 128, 129.7, 131.3, 142.2, 174.6.

EXAMPLE 11. (R)-DIDESMETHYLSIBUTRAMINE (D)-TARTRATE

Resolution from Didesmethylsibutramine Free Base

A method of isolating the (D)-tartrate salt of (R)-didesmethylsibutramine ((R)-DDMA•(D)-TA) from racemic didesmethylsibutramine free base is shown in Scheme 9A and described in detail below:

Scheme 9A

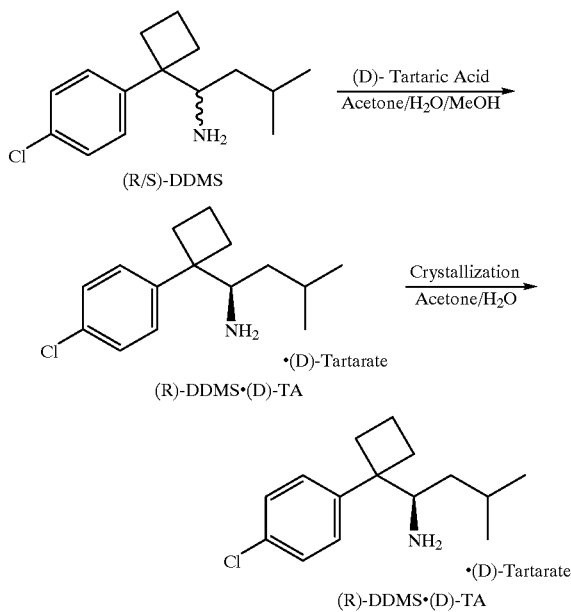

Following Scheme 9A, a mixture of (R/S)-didesmethylsibutramine (20.3 g), acetone/water/methanol (350 mL, 1:0.13:0.7, v:v:v), and (D)-tartaric acid (12.1 g) were added to a 500 mL three-necked round bottom. The reaction mixture was heated to reflux for 30 minutes and then cooled to 45° C. The reaction mixture was then seeded with (R)-DDMA•(D)-TA (10 mg; 99.6% ee) and stirred at 40–45° C. for 30 minutes. The mixture was then cooled to room temperature and stirred for 1 hour. The resulting slurry was then filtered and the wet cake was washed with cold acetone/water and dried to give 10.3 g (33%) of (R)-DDMA•(D)-TA (90% ee).

Resolution from (R/S)-Didesmethylsibutramine (D)-tartrate

A method of isolating the (D)-tartrate salt of (R)-didesmethylsibutramine ((R)-DDMA•(D)-TA) from the (D)-tartrate salt of racemic didesmethylsibutramine is shown in Scheme 9B and described in detail below:

Scheme 9B

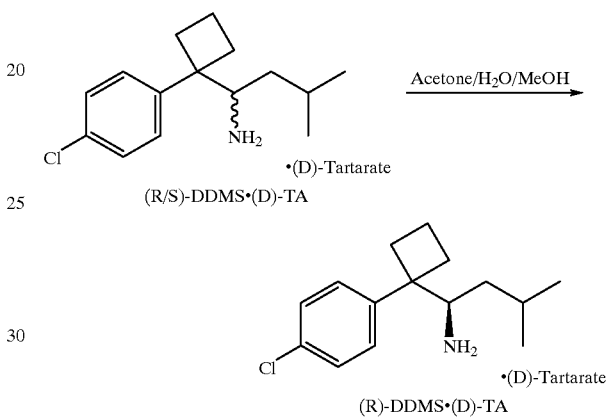

Following Scheme 9B, a mixture of (R/S)-didesmethylsibutramine•(D)-TA (5.0 g) in acetone (50 mL), water (6.7 mL), and methanol (3.3 mL) was refluxed for 30 minutes. The mixture was then cooled to room temperature and the resulting slurry was filtered to provide a wet cake which was then washed with cold acetone and dried to give (R)-DDMA•(D)-TA (1.4 g, 28%; 92% ee).

Enrichment of (D)-Tartrate Salt of (R)-DDMS

A mixture of (R)-DDMA•(D)-TA (25 g, 92% ee) and acetonitrile/water/ethanol (300 mL:65 mL:30 mL) was refluxed for 1 hour. The mixture was then cooled to room temperature to provide a slurry which was filtered and dried to give (R)-DDMS-(D)-TA (18 g, 71.3%; 99.7% ee; and 99.91% chemical purity). NMR (DMSO-d$_6$): $^1$H ( d), 0.7–0.9 (m, 6H), 0.9–1.05 (t, 1H), 1.1–1.24 (b, 1H), 1.5–1.8 (b, 2H), 1.8–2.02 (b, 1H), 2.1–2.4 (3, 3H), 2.4–2.6 (b, 1H), 3.5 (m, 1H), 4.0 (s, 2H), 7.1–7.6 (m, 4H, with 6H from NH$_2$, OH and COOH). $^{13}$C (d): 15.4, 21.5, 22.0, 22.2, 32.0, 32.2, 38.4, 49.0, 54.0, 72.8, 128.8, 130.0, 132.0, 143.0, 175.5.

EXAMPLE 12. (S)-DIDESMETHYLSIBUTRAMINE (L)-TARTRATE

A method of isolating the (L)-tartrate salt of (S)-didesmethylsibutramine ((S)-DDMS-(L)-TA) from racemic didesmethylsibutramine free base is shown in Scheme 10 and described in detail below:

Scheme 10

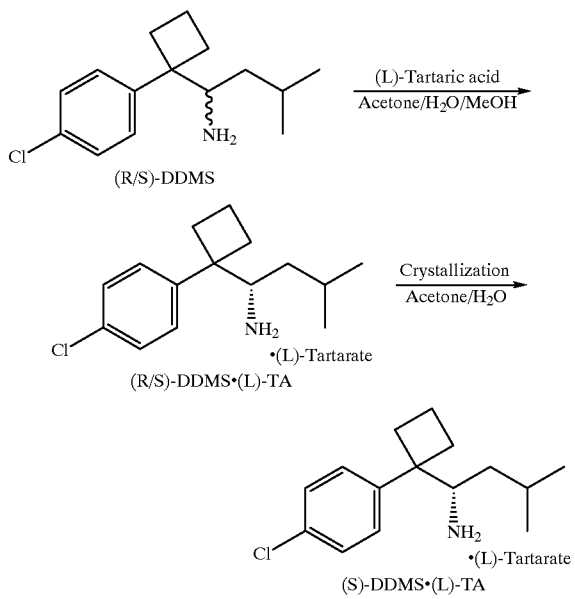

Formation of (L)-Tartrate Salt of (S)-DDMS (R/S) Didesmethylsibutramine (20.5 g), acetone/water/methanol (350 mL, 1:0.13:0.7, v:v:v) and (L)-tartaric acid (12.2 g) were added to a 500 mL three-necked round bottom flask. The mixture was heated to reflux for 30 minutes and then cooled to 45 °C. The reaction mixture was then seeded with (S)-DDMS-(L)-TA (10 mg and 99.7% ee) and stirred at 40–45 °C. for 30 minutes. The mixture was cooled to room temperature and stirred for 1 hour. The resulting slurry was filtered to provide a wet cake, which was washed with cold acetone/water and dried to give 10.8 g (33.4%) of (S)-DDMS-(L)-TA (89.7% ee).

Preparation of (L)-Tartrate Salt of (S)-DDMS from Mother Liquor of (R)-DDMS-(D)-TA A solution of DDMS tartrate in acetone/water/methanol (mother liquor of (R)-DDMS-(D)-TA) was concentrated to remove acetone and methanol. The residue was treated with aqueous NaOH (3N, 150 mL) and extracted with ethyl acetate. The organic phase was washed with water (100 mL) and concentrated to give didesmethylsibutramine free base (45 g, 0.18 mol and 36% ee of (S)-isomer). The free amine was charged with (L)-tartaric acid (53.6 g, 0.35 mol), acetone (600 mL), water (80 mL), and methanol (40 mL). The mixture was heated to reflux for 1 hour and then cooled to room temperature. The resulting slurry was filtered to provide a wet cake, which was then washed with cold acetone/water two times to give 26.7 g (56% based on (S)-didesmethylsibutramine) of (S)-DDMS-(L)-TA (96% ee).

Enrichment of (S)-DDMS-(L)-TA

A mixture of (S)-DDMA•(L)-TA (26.7 g) in acetonitrile/water (475 mL; 1:0.2, v:v) was refluxed for 1 hour and then cooled to room temperature. The resulting slurry was filtered and dried to give 17.4 g (65%) of (S)-DDMS-(L)-TA (99.9% ee; 99.94% chemical purity). NMR (DMSO-$d_6$): $^1$H ( d), 0.7–0.9 (m, 6H), 0.9–1.05 (m, 1H), 1.1–1.3 (b, 1H), 1.52–1.8 (b, 2H), 1.84–2.05 (b, 1H), 2.15–2.4 (b, 3H), 2.4–2.6 (b, 1H), 3.65–3.58 (m, 1H), 4.0 (s, 2H), 6.7–7.3 (b, 6H from NH2, OH and COOH) 7.1–7.6 (m, 4H). $^{13}$C (d): 15.4, 21.5, 22.0, 22.2, 32.0, 32.2, 38.4, 49.0, 54.0, 72.8, 128.8, 130.0, 132.0, 143.0, 175.5.

EXAMPLE 13: DETERMINATION OF POTENCY AN SPECIFICITY

A pharmacologic study is conducted to determine the relative potency, comparative efficacy, binding affinity, and toxicity of the racemic mixture of sibutramine, its enantiomers, the metabolites of sibutramine, and their enantiomers. The profile of relative specificity of monoamine reuptake inhibition is determined from the compounds' inhibition of norepinephrine (NE) reuptake in brain tissue with that of the inhibition of dopamine (DA) and serotonin (5HT) reuptake.

High-affinity uptake of the $^3$H-radiomonoamines is studied in synaptosomal preparations prepared from rat corpus striatum (for inhibition of DA reuptake) and cerebral cortex (for 5HT and NE) using methods published by Kula et al., *Life Sciences* 34(26): 2567–2575, 1984, and Baldessarini et al., *Life Sciences* 39:1765–1777, 1986. Tissues are freshly dissected on ice and weighed. Following homogenization by hand (14 strokes in 10–35 vols of ice-cold isotonic 0.32M sucrose, containing nialamide, 34 µM) in a Teflon-on-glass homogenizer, the tissue is centrifuged for ten minutes at 900×g; the supernatant "solution" that results contains synaptosomes that are used without further treatment. Each assay tube contains 50 µL of the cerebral homogenate, radiolabelled-$^3$H-monoamine, and the test compound (e.g., the pure sibutramine enantiomers, the racemate, and appropriate standards) in a freshly prepared physiologic buffer solution with a final volume of 0.5 mL. Tissues are preincubated for 15 minutes at 37° C. before the assay. Tubes are held on ice until the start of incubation, which is initiated by adding $^3$H-amine to provide a final concentration of 0.1 µM. Tubes are incubated at 37° C. for 10 minutes with $^3$H-DA (26 Ci/mmol) and for 20 minutes with $^3$H-5HT (about 20 Ci/mmol) and $^3$H-NE (about 20 Ci/mmol). The specific activity of the radiomonoamine will vary with available material and is not critical. The reaction is terminated by immersion in ice and dilution with 3 mL of ice cold isotonic saline solution containing 20 mM TRIS buffer (pH 7.0). These solutions are filtered through cellulose ester microfilters, followed by washing with two 3 mL volumes of the same buffer. The filter is then counted for $^3$H-radioactivity in 3.5 mL of Polyfluor at about 50% efficiency for tritium. Blanks (either incubated at 0° C. or incubated with specific, known uptake inhibitors of DA [GRB-12909, 10 µM], 5HT- [zimelidine 10 µM], or of NE [desipramine 10 µM]) are usually indistinguishable from assays performed without tissue and average 2–3% of total CPM.

Comparison of the amounts of $^3$H-radioactivity retained on the filters provides an indication of the relative abilities of the pure enantiomers and racemic mixture of sibutramine (and of known DA, 5-HT, and NE reuptake inhibitors) to block the reuptake of these monoamines in those tissues. This information is useful in gauging the relative potency and efficacy of compounds of the invention (e.g., dopamine reuptake inhibitors, such as a racemic or optically pure sibutramine metabolite, and 5-HT$_3$ antagonists).

The acute toxicities of the compounds of the invention are determined in studies in which rats are administered progressively higher doses (mg/kg) of the pure isomers or racemate. That lethal dose which, when administered orally, causes death of 50% of the test animals, is reported as the LD$_{50}$. Comparison of LD$_{50}$ values for the enantiomers and racemate provides a measure of the relative toxicity of the compositions.

EXAMPLE 14: BINDING AFFINITIES

The binding affinities of racemic and optically pure sibutramine ((R/S)-, (R)-, and (S)-sibutramine), desmethylsibutramine ((R/S)-, (R)-, and (S)-desMe), and didesmethylsibutramine ((R/S)-, (R)-, and (S)-didesMe) were determined at the nonselective muscarinic receptor and the serotonin (5-HT) uptake site from rat cerebral cortex, the human recombinant norepinephrine (NE) uptake site, and the $\beta_3$-receptor from rat adipose tissue. Compounds were tested initially at 10 µm in duplicate, and if ≧50% inhibition of specific binding was observed, they were tested further at 10 different concentrations in duplicate in order to obtain full competition curves. IC$_{50}$ values (concentration required to inhibit 50% specific binding) were then determined by nonlinear regression analysis of the curves and tabulated below.

| Compound | Muscarinic Receptor | Binding IC$_{50}$ Values (nM) | | 5-HT Selectivity (NE/5-HT) |
|---|---|---|---|---|
| | | NE Uptake | 5-HT Uptake | |
| (R/S)-Sibutramine | 2,650 | 350 | 2,800 | 1,200 |
| (R)-Sibutramine | 4,010 | 110 | 2,100 | 650 |
| (S)-Sibutramine | 3,020 | 2,500 | 4,900 | 1,500 |
| (R/S)-desMe | 1,170 | 10 | 21 | 19 |
| (R)-desMe | — | 4 | 44 | 12 |
| (S)-desMe | 654 | 870 | 9,200 | 180 |
| (R/S)-didesMe | — | 16 | 63/14 | 39/26 |
| (R)-didesMe | — | 13 | 140 | 8.9 |
| (S)-didesMe | — | 6.2 | 4,300 | 12 |
| Atropine | 0.31 | — | — | — |
| GBR 1909 | — | — | — | 5.6/2.6 |
| Imipramine | — | — | 145/32 | — |
| Protriptyline | — | 3.6/0.9 | — | — |
| Zimelidine | — | — | 129 | — |

None of the compounds showed more than 15% inhibition of binding at the $\beta_3$-receptor, and affinity for the muscarinic site was weak compared to atropine. Further, binding to the NE and 5-HT uptake sites was orders of magnitude less than that of the standards.

The above data, which was generated as described above in Example 13, shows that (R)-desmethylsibutramine and (R)-didesmethylsibutramine are potent inhibitors of NE uptake and 5-HT uptake, but have negligible activity at muscarinic receptors.

EXAMPLE 15: ORAL FORMULATION

Hard gelatin capsule dosage forms that are lactose-free comprising sibutramine metabolites can be prepared using the following ingredients:

| Component | 5 mg capsule | 10 mg capsule | 20 mg capsule |
|---|---|---|---|
| Racemic or optically pure sibutramine metabolite | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The racemic or optically pure sibutramine metabolite is sieved and blended with the excipients listed. The mixture is filled into suitably sized two-piece hard gelatin capsules using suitable machinery and methods well known in the art. See, e.g., *Remington's Pharmaceutical Sciences*, 16th or 18th Editions, each incorporated herein in its entirety by reference. Other doses can be prepared by altering the fill weight and, if necessary, changing the capsule size to suit. Any of the stable, non-lactose hard gelatin capsule formulations above can be formed.

Compressed tablet dosage forms of sibutramine metabolites can be prepared using the following ingredients:

| Component | 5 mg capsule | 10 mg capsule | 20 mg capsule |
|---|---|---|---|
| Racemic or optically pure sibutramine metabolite | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The racemic or optically pure sibutramine metabolite is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths can be prepared by altering the ratio of the active ingredient to the excipient(s) or modifying the table weight.

The embodiments of the invention described above are intended to be merely exemplary and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating or preventing sexual dysfunction which comprises administering to a patient in need of such treatment or prevention therapeutically or prophylactically effective amounts of a sibutramine metabolite, or a pharmaceutically acceptable salt, solvate, hydrate, clathrate, or prodrug thereof, and a phosphodiesterase inhibitor.

2. The method of claim 1 wherein the sibutramine metabolite is optically pure.

3. The method of claim 2 wherein the sibutramine metabolite is (R)-desmethylsibutramine, (S)-desmethylsibutramine, (R)-didesmethylsibutramine, or (S)-didesmethylsibutramine.

4. The method of claim 1 wherein the phosphodiesterase inhibitor is a PDE5 or PDE6 inhibitor.

5. The method of claim 4 wherein the phosphodiesterase inhibitor is sildenophil, desmethylsildenophil, vinopocetine, milrinone, amrinone, pimobendan, cilostamide, enoximone, peroximone, vesnarinone, rolipram, R020–1724, zaprinast, dipyridamole, or a pharmaceutically acceptable salt, solvate, hydrate, clathrate, prodrug, optically and pharmacologically active stereoisomer, or a pharmacologically active metabolite thereof.

6. The method of claim 1 wherein the amount of sibutramine metabolite administered is from about 0.1 mg to about 60 mg/day.

7. The method of claim 6 wherein the amount of sibutramine metabolite administered is from about 2 mg to about 30 mg/day.

8. The method of claim 7 wherein the amount of sibutramine metabolite administered is from about 5 mg to about 15 mg/day.

9. The method of claim 1 wherein the sibutramine metabolite and/or the phosphodiesterase inhibitor is administered transdermally or mucosally.

10. The method of claim 1 wherein the patient is male.

11. The method of claim 10 wherein the sexual dysfunction is erectile dysfunction.

12. The method of claim 1 wherein the patient is female.

* * * * *